United States Patent
Auf Der Maur et al.

(10) Patent No.: US 8,936,785 B2
(45) Date of Patent: Jan. 20, 2015

(54) SCFV ANTIBODIES WHICH PASS EPITHELIAL AND/OR ENDOTHELIAL LAYERS

(75) Inventors: Adrian Auf Der Maur, Dietikon (CH); Alcide Barberis, Olivone (CH); David M. Urech, Mannedorf (CH); Peter Lichtlen, Adliswil (CH)

(73) Assignee: Esbatech, An Alcon Biomedical Research Unit, LLC (CH)

( * ) Notice: Subject to any disclaimer, the term of this patent is extended or adjusted under 35 U.S.C. 154(b) by 1053 days.

(21) Appl. No.: 12/307,875

(22) PCT Filed: Jul. 10, 2007

(86) PCT No.: PCT/CH2007/000334
§ 371 (c)(1), (2), (4) Date: Jul. 30, 2009

(87) PCT Pub. No.: WO2008/006235
PCT Pub. Date: Jan. 17, 2008

(65) Prior Publication Data
US 2009/0311251 A1   Dec. 17, 2009

Related U.S. Application Data

(60) Provisional application No. 60/899,907, filed on Feb. 6, 2007, provisional application No. 60/819,378, filed on Jul. 10, 2006.

(51) Int. Cl.
*A61K 39/395* (2006.01)
*C07K 16/18* (2006.01)
(Continued)

(52) U.S. Cl.
CPC ........... *C07K 16/18* (2013.01); *A61K 39/39591* (2013.01); *C07K 16/22* (2013.01);
(Continued)

(58) Field of Classification Search
None
See application file for complete search history.

(56) References Cited

U.S. PATENT DOCUMENTS

| 4,079,038 A | 3/1978 | Choi et al. |
| 4,093,709 A | 6/1978 | Choi et al. |

(Continued)

FOREIGN PATENT DOCUMENTS

| CA | 2379661 A1 | 9/2003 |
| WO | WO-00/40262 | 7/2000 |

(Continued)

OTHER PUBLICATIONS

Bos et al., Exp Dermatol 2000: 9: 165-169.*

(Continued)

*Primary Examiner* — Zachary Skelding

(57) ABSTRACT scFv antibodies which specifically bind selected antigens and are obtainable by a method comprising (i) selecting from a pool of soluble and stable antibody frameworks a soluble and stable framework matching best the framework of a non-human antibody against the antigen with a certain binding specificity, (ii) either providing said soluble and stable framework with CDRs that bind specifically to said antigen, or mutating the framework of said non-human antibody towards the sequence of said soluble and stable framework, to generate scFv antibodies, (iii) testing the generated antibody for solubility and stability, and testing the generated antibody for antigen binding, and (iv) selecting an scFV that is soluble, stable and binds to the antigen specifically. Also provided are pharmaceutical compositions comprising said scFv antibody, methods of treatment and diagnosis for diseases related to over expression of antigens that are specifically bound by said antibody.

3 Claims, 15 Drawing Sheets

(51) Int. Cl.
  *C07K 16/22* (2006.01)
  *C07K 16/24* (2006.01)
  *A61K 39/00* (2006.01)

(52) U.S. Cl.
  CPC ........ *C07K 16/241* (2013.01); *A61K 2039/505* (2013.01); *A61K 2039/54* (2013.01); *C07K 2317/24* (2013.01); *C07K 2317/622* (2013.01)
  USPC .................................................... 424/145.1

(56) References Cited

U.S. PATENT DOCUMENTS

| | | | |
|---|---|---|---|
| 4,131,648 A | 12/1978 | Choi et al. | |
| 4,138,344 A | 2/1979 | Choi et al. | |
| 4,180,646 A | 12/1979 | Choi et al. | |
| 4,304,767 A | 12/1981 | Heller et al. | |
| 4,946,931 A | 8/1990 | Heller et al. | |
| 5,968,543 A | 10/1999 | Heller et al. | |
| 6,413,536 B1 | 7/2002 | Gibson et al. | |
| 6,596,296 B1 | 7/2003 | Nelson et al. | |
| 6,613,355 B2 | 9/2003 | Ng et al. | |
| 6,667,371 B2 | 12/2003 | Ng et al. | |
| 8,067,547 B2 * | 11/2011 | Ewert et al. | 530/387.3 |
| 2003/0165545 A1 * | 9/2003 | Huth et al. | 424/400 |
| 2006/0062758 A1 | 3/2006 | Cui et al. | |
| 2007/0141092 A1 * | 6/2007 | Xia et al. | 424/400 |
| 2007/0178103 A1 * | 8/2007 | Fey et al. | 424/155.1 |

FOREIGN PATENT DOCUMENTS

| | | |
|---|---|---|
| WO | WO-01/48017 | 7/2001 |
| WO | WO-03/097697 | 11/2003 |
| WO | 2005091853 A2 | 10/2005 |
| WO | 2006039638 A2 | 4/2006 |
| WO | 2006124451 A2 | 11/2006 |
| WO | WO 2006131013 A2 * | 12/2006 |
| WO | 2008006235 A2 | 1/2008 |
| WO | WO-2008/006235 | 1/2008 |

OTHER PUBLICATIONS

Auf der Maur, "Antigen-independent selection of intracellular stable antibody frameworks," *Methods*, 34:215-224 (2004).
Brereton et al., "Influence of format on in vitro penetration of antibody fragments through porcine cornea," *Br J Ophthalmol*, 89:1205-1209 (2005).
El-Shabrawi et al., "Anti-tumor Necrosis Factor-alpha Therapy with Infliximab as an Alternative to Corticosteroids in the Treatment of Human Leukocyte Antigen B27-associated Acute Anterior Uveitis," *American Academy of Ophthalmology*, 109(12):2342-2346 (2002).
Lindstedt et al., "Anti-TNF-α therapy for sight threatening uveitis," *Br J Ophthalmol*, 89:533-536 (2005).
Thiel et al., "Penetration of engineered antibody fragments into the eye," *Clin Exp Immunol*, 128:67-74 (2002).
Barberis; Selection of highly stable human antibody fragments for compartmental therapeutic approaches; Human Antibodies; vol. 13; No. 1-2; pp. 22; Oct. 9, 2004.
Alfthan et al.; "Properties of a single-chain antibody containing different linker peptides"; Protein Engineering; vol. 8; No. 7; pp. 725-731 (1995).
Altschul et al.; "Basic local alignment search tool"; J. Mol. Biol.; vol. 215; pp. 403-410 (1990).
Altschul et al.; "Gapped BLAST and PSI-BLAST: a new generation of protein database search programs"; Nucleic Acids Research; vol. 25; No. 17; pp. 3389-2402 (1997).
Auf Der Maur et al.; "Antigen-independent selection of stable intracellular single-chain antibodies"; FEBS Letters; vol. 508; pp. 407-412 (2001).
Auf Der Maur et al.; "Direct in vivo screening of intrabody libraries constructed on a highly stable single-chain framework"; The Journal of Biological Chemistry; vol. 277; No. 47; pp. 45075-45085 (2002).

Benitez-Del-Castillo et al.; Long-term treatment of refractory posterior uveitis with anti-TNF alpha (infliximab); Eye; vol. 19; pp. 841-845 (2005).
Binz et al.; "Engineering novel binding proteins from nonimmunoglobulin domains"; Nature Biotechnology; vol. 23; No. 10; pp. 1257-1268 (Oct. 2005).
Bird et al.; "Single-chain antigen-binding proteins"; Science; vol. 242; pp. 423-426 (Oct. 21, 1988).
Bonfioli and Orefice; "Behcet's Disease"; Seminars in Ophthalmology; vol. 20; pp. 199-206 (2005).
Boyd et al.; "Immunopathology of a noninfectious posterior and intermediate uveitides"; Survey of Ophthalmology; vol. 46; No. 3; pp. 209-233 (2001).
Chothia et al.; "Domain association in immunoglobulin molecules (the packing of variable domains)"; J. Mol. Biol; vol. 186; pp. 651-663 (1985).
Chothia and Lesk; "Canonical structures for the hypervariable regions of immunoglobulins"; J. Mol. Biol; vol. 196; pp. 901-917 (1987).
Degim and Celebi; "Controlled delivery of peptides and proteins"; Current Pharmaceutical Design; vol. 13; pp. 99-117 (2007).
Dick et al.; "Immunosuppressive therapy for chronic uveitis: optimising therapy with steroids and cyclosporin A"; British Journal of Ophthalmology; vol. 81; pp. 1107-1112 (1997).
Direskeneli; Behcet's disease: infectious aetiology, new autoantigens, and HLA-B51; Ann. Rheum. Dis; vol. 60; pp. 996-1002 (2001).
Doring et al.; "Identifidcation and characterization of a TNF alpha antagonist derived form a monoclonal antibody"; Molecular Immunology; vol. 31; No. 14; pp. 1059-1067 (1994).
El-Shabrawi et al.; "Anti-tumour necrosis factor alpha treatment in chronic recurrent inflammation of the anterior segment of the eye in patients resistant to standard immunomodulatory treatment"; Ann Rheum Dis.; vol. 62; pp. 1243-1244 (2003).
Evereklioglu; Current concepts in the etiology and treatment of Behcet Disease; Survey of Ophthalmology; vol. 50; No. 4; pp. 297-350; (Jul.-Aug. 2005).
Winter and Milstein; "Man-made antibodies"; Nature; vol. 349; pp. 293-299 (Jan. 24, 1991).
Giansanti et al.; "Infliximab for the treatment of posterior uveitis with retinal neovascularization in Behcet disease"; European Journal of Ophthalmology; vol. 14; No. 5; pp. 445-448 (2004).
Glockshuber et al.; "A comparison of strategies to stabilize immunoglobulin Fv-fragments"; Biochemistry; vol. 29; pp. 1362-1367 (1990).
Grell, et al.; "The transmembrane form of tumor necrosis factor is the prime activating ligand of the 80 kDa tumor necrosis factor receptor"; Cell; vol. 83; pp. 793-802 (Dec. 1, 1995).
Holliger and Hudson; "Engineered antibody fragments and the rise of single domains"; Nature Biotechnology; vol. 23; No. 9; pp. 1126-1136 (Sep. 7, 2005).
Huston et al.; "Protein engineering of antibody binding sites: recovery of specific activity in an anti-digoxin single-chain Fv analogue produced in *Escherichia coli*"; Proc. Natl. Acad. Sci.; vol. 85; pp. 5879-5883 (Aug. 1988).
Johnson and Quay; "Advances in nasal drug delivery through tight junction technology"; Expert Opinion Drug Delivery; vol. 2; No. 2; pp. 281-298 (2005).
Joseph et al.; "Infliximab in the treatment of refractory posterior uveitis"; Ophthalmology; vol. 110; pp. 1449-1453 (2003).
Korz et al.; "Simple fed-batch technique for sigh cell density cultivation of *Escherichia coli*"; Journal of Biotechnology; vol. 39; pp. 59-65 (1995).
Kotter et al.; "Human recombinant interferon alfa-2a for the treatment of Behcet's disease with sight threatening posterior or panuveitis"; Br. J. Ophthalmol.; vol. 87; pp. 423-431 (2003).
Lamoya and Nisonoff; "Preparation of F(ab')2 fragments from mouse IgG of various subclasses"; Journal of Immunological Methods; vol. 56; pp. 235-243 (1983).
Lanthier et al.; "Infliximab in the treatment of posterior uveitis in Behcet's disease"; Presse Med.; vol. 34; pp. 916-918 (2005).
Lightman and Kok; "Developments in the treatment of uveitis"; Expert Opinion; vol. 11; No. 1; pp. 59-67 (2002).

(56) References Cited

OTHER PUBLICATIONS

Matthew and Reichardt; "Development and application of an efficient procedure for converting mouse IgM into small, active fragments"; Journal of Immunological Methods; vol. 50; pp. 239-253 (1982).

Murphy et al.; "Neutralizing tumor necrosis factor activity leads to remission in patients with refractory noninfectious posterior uveitis"; Arch Ophthalmol; vol. 122; pp. 845-851 (2004).

Neddleman and Wunsch; "A general method applicable to the search for similarities in the amino acid sequence of two proteins"; J. Mol. Biol.; vol. 48; pp. 443-453 (1970).

Ohno et al.; "Efficacy, safety, and pharmacokinetics of multiple administration of infliximab in Behcet's disease with refractory uveoretinitis"; The Journal of Rheumatology; vol. 31; No. 7; pp. 1362-1368 (2004).

Ozen; "Vasculopathy, Behcet's syndrome, and familial Mediterranean fever"; Current Opinion Rheum; vol. 11; pp. 393-398 (1999).

Parham et al.; "Monoclonal antibodies: purification, fragmentation and application to structural and functional studies of Class I MHC antigens"; Journal of Immunological Methods; vol. 53; pp. 133-173 (1982).

Parham; On the fragmentation of monoclonal IgG1, IgG2a and IgG2b from BALB/c Mice; The Journal of Immunology; vol. 131; No. 6; pp. 2895-2902 (Dec. 1983).

Perez-Guijo et al.; "Tumour necrosis factor-alpha levels in aqueous humour and serum from patients with uveitis: the involvement of HLA-B27"; Current Medical Research and Opinion; vol. 20; No. 2; pp. 155-157 (2004).

Power et al.; "Outcomes in anterior uveitis associated iwth the HLA-B27 haplotype"; Ophthalmology; vol. 105; pp. 1646-1651 (1998).

Powers et al.; "Pleiotrophin signaling through anaplastic lymphoma kinase is rate-limiting for glioblastoma growth"; The Journal of Biological Chemistry; vol. 277; No. 16; pp. 14153-14158 (Apr. 19, 2002).

Reiff et al.; "Etanercept therapy in children with treatment-resistant uveitis"; Arthritis and Rheumatism; vol. 44; No. 6; pp. 1411-1415 (Jun. 2001).

Rosenbaum; "Blind insight: eyeing anti-tumor necrosis factor treatment in uveitis associated with Behcet's disease"; The Journal of Rheumatology; vol. 31; No. 7; pp. 1241-1243 (2004).

Sakane et al.; "Behcet's disease"; The New England Journal of Medicine; vol. 341; pp. 1284-1291 (Oct. 21, 1999).

Schaerer-Brodbeck and Barberis; "Coupling homologous recombination with growth selection in yeast: a tool for construction of random DNA sequence libraries"; Biotechniques; vol. 37; No. 2; pp. 202-206 (2004).

Sfikakis et al.; "Effect of infliximab on sight-threatening panuveitis in Behcet's disease"; Research Letters; The Lancet: vol. 358; pp. 295-296 (Jul. 28, 2001).

Stocks; "Intrabodies: production and promise"; Reviews; Drug Discovery Today; vol. 9; No. 22; pp. 960-966 (Nov. 2004).

Suhler et al.; "A prospective trial of infliximab therapy for refractory uveitis"; Arch Ophthalmol.; vol. 123; pp. 903-912 (2005).

Sultana et al.; "Advances in the topical ocular drug delivery"; Expert Rev. Ophthalmol.; vol. 2; No. 2; pp. 309-323 (2007).

Tugal-Tutkun et al.; "Uveitis in Behcet disease: an analysis of 880 patients"; Am J Ophthalmol; vol. 138; pp. 373-380 (2004).

Tugal-Tutkun et al.; "Efficacy of infliximab in the treatment of uveitis that is resistant to treatment with the combination of azathioprine, cyclosporine, and corticosteroids in Behcet's disease"; Arthritis & Rheumatism; vol. 52; No. 8; pp. 2478-2484 (Aug. 2005).

Tursen et al.; "Evaluation of clinical findings according to sex in 2313 Turkish patients with Behcet's disease"; International Journal of Dermatology; vol. 42; pp. 346-351 (2003).

Valente et al.; "Second virial coefficient studies of cosolvent-induced protein self-interaction"; Biophysical Journal; vol. 89; pp. 4211-4218 (Dec. 2005).

Verity et al.; "HLA and tumour necrosis factor (TNF) polymorphisms in ocular Behcet's disease"; Tissues Antigens; vol. 54; pp. 264-272 (1999).

Verity et al.; "Behcet's disease, the silk road and HLA-B51: historical and geographical perspectives"; Tissue Antigens; vol. 54; pp. 213-220 (1999).

Wang and Lee; "High cell density culture of metabolically engineered *Escherichia coli* for the productin of Poly(3-hydroxybutyrate) in a defined medium"; Biotechnol Bioeng; vol. 58; pp. 325-328 (1998).

Ward et al.; "Binding activities of a repertoire of single immunoglobulin variable domains secreted form *Escherichia coli*"; Letters to Nature; Nature; vol. 341; pp. 544-546 (Oct. 12, 1989).

Wechsler et al.; "Infliximab in refractory uveitis due to Behcet's disease" Clinical and Experimental Rheumatology; vol. 22; Suppl. 34; pp. S14-S16 (2004).

Worn et al.; "Correlation between in vitro stability and in vivo performance of anti-GCN4 intrabodies as cytoplasmic inhibitors"; The Journal of Biological Chemistry; vol. 274; No. 4; pp. 2795-2803 (Jan. 28, 2000).

Yurdakul et al.; "Behcet syndrome"; Current Opinion in Rheumatology; vol. 16; pp. 38-42 (2004).

Zierhut et al.; "Human genome and diseases: Review Immunology and functional geonomics of Behcet's disease"; CMLS Cellyular and Molecular Life Sciences; vol. 60; pp. 1902-1922 (2003).

Liu et al.; "One-step on-column purification and refolding of a single-chain variable fragment (scFv) antibody against tumour necrosis factor α"; Biotechnol. Appl. Biochem.; (2006); No. 43, pp. 137-145.

Ka Williams et al.; "Topically applied antibody fragments penetrate into the back of the rabbit eye"; Nature Publishing Group (www.nature.com/eye); 2005; No. 19; pp. 910-913.

\* cited by examiner

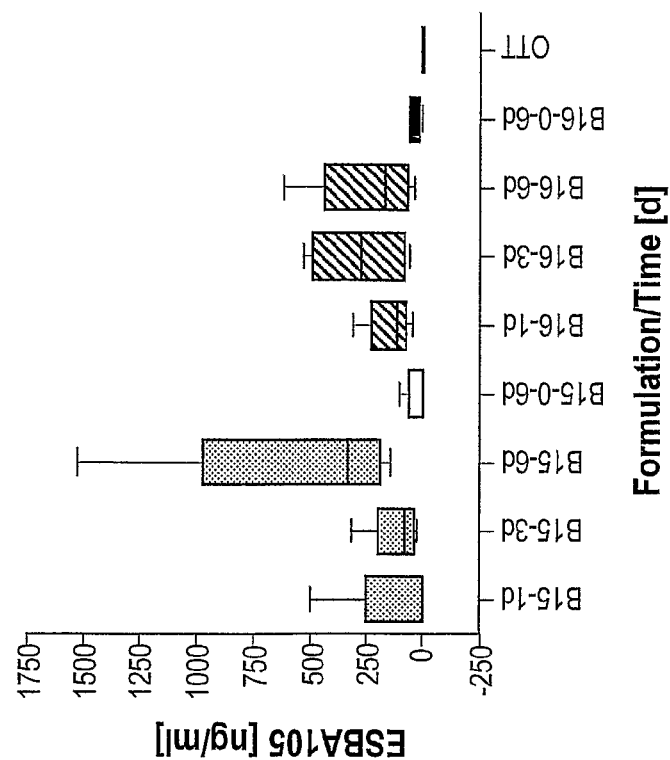
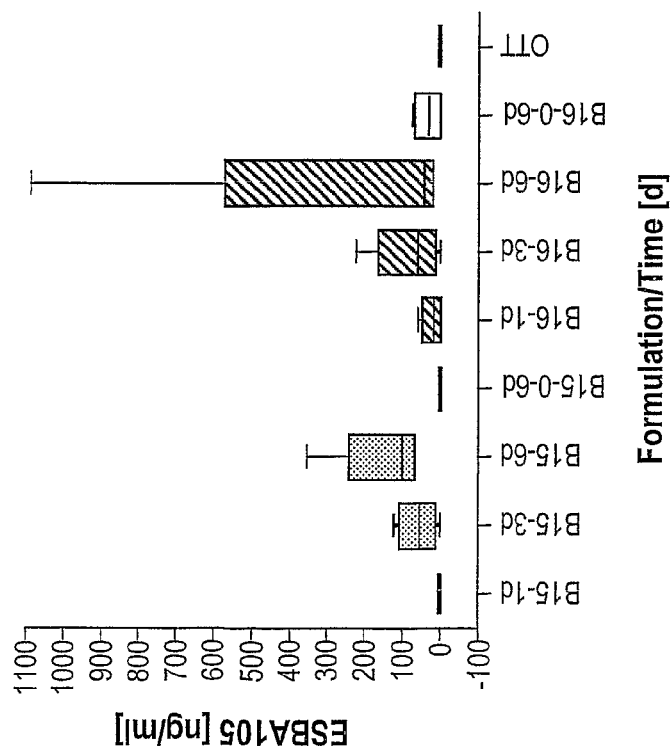
Fig. 11a
Fig. 11b

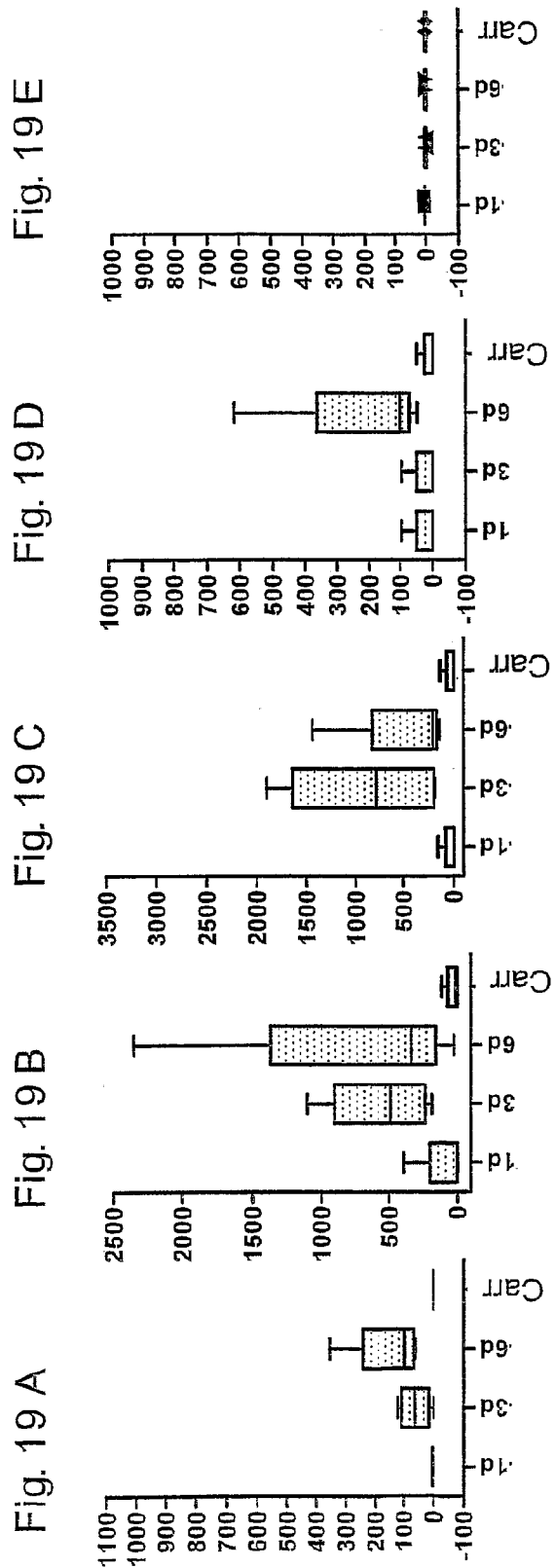

SEQUENCE LISTING

```
<160> NUMBER OF SEQ ID NOS: 22

<210> SEQ ID NO 1
<211> LENGTH: 107
<212> TYPE: PRT
<213> ORGANISM: Artificial
<220> FEATURE:
<223> OTHER INFORMATION: Synthetic peptide

<400> SEQUENCE: 1

Glu Ile Val Met Thr Gln Ser Pro Ser Thr Leu Ser Ala Ser Val Gly
1               5                   10                  15

Asp Arg Val Ile Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Ala Glu Phe Thr Leu Thr Ile Ser Ser Leu Gln Pro
65                  70                  75                  80

Asp Asp Phe Ala Thr Tyr Tyr Cys Gln Gln Tyr Lys Ser Tyr Trp Thr
                85                  90                  95

Phe Gly Gln Gly Thr Lys Leu Thr Val Leu Gly
            100                 105

<210> SEQ ID NO 2
<211> LENGTH: 108
<212> TYPE: PRT
<213> ORGANISM: Artificial
<220> FEATURE:
<223> OTHER INFORMATION: Synthetic peptide

<400> SEQUENCE: 2

Glu Ile Val Leu Thr Gln Ser Pro Ser Ser Leu Ser Ala Ser Val Gly
1               5                   10                  15

Asp Arg Val Thr Leu Thr Cys Arg Ala Ser Gln Gly Ile Arg Asn Glu
            20                  25                  30

Leu Ala Trp Tyr Gln Gln Arg Pro Gly Lys Ala Pro Lys Arg Leu Ile
        35                  40                  45

Tyr Ala Gly Ser Ile Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Val Ala Val Tyr Tyr Cys Gln Gln Tyr Tyr Ser Leu Pro Tyr
                85                  90                  95

Met Phe Gly Gln Gly Thr Lys Val Asp Ile Lys Arg
            100                 105

<210> SEQ ID NO 3
<211> LENGTH: 109
<212> TYPE: PRT
<213> ORGANISM: Artificial
<220> FEATURE:
<223> OTHER INFORMATION: Synthetic peptide

<400> SEQUENCE: 3
```

-continued

Glu Ile Val Met Thr Gln Ser Pro Ala Thr Leu Ser Val Ser Pro Gly
1               5                   10                  15

Glu Ser Ala Ala Leu Ser Cys Arg Ala Ser Gln Gly Val Ser Thr Asn
            20                  25                  30

Val Ala Trp Tyr Gln Gln Lys Pro Gly Gln Ala Pro Arg Leu Leu Ile
        35                  40                  45

Tyr Gly Ala Thr Thr Arg Ala Ser Gly Val Pro Ala Arg Phe Ser Gly
    50                  55                  60

Ser Gly Ser Gly Thr Glu Phe Thr Leu Thr Ile Asn Ser Leu Gln Ser
65                  70                  75                  80

Glu Asp Phe Ala Ala Tyr Tyr Cys Gln Gln Tyr Lys His Trp Pro Pro
                85                  90                  95

Trp Thr Phe Gly Gln Gly Thr Lys Val Glu Ile Lys Arg
                100                 105

<210> SEQ ID NO 4
<211> LENGTH: 108
<212> TYPE: PRT
<213> ORGANISM: Artificial
<220> FEATURE:
<223> OTHER INFORMATION: Synthetic peptide

<400> SEQUENCE: 4

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Thr Leu Thr His Tyr
            20                  25                  30

Leu Ala Trp Tyr Gln Gln Lys Pro Gly Gln Ala Pro Arg Leu Leu Ile
        35                  40                  45

Tyr Asp Thr Ser Lys Arg Ala Thr Gly Thr Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Ser Ala Leu Tyr Tyr Cys Gln Gln Arg Asn Ser Trp Pro His
                85                  90                  95

Thr Phe Gly Gly Gly Thr Lys Leu Glu Ile Lys Arg
                100                 105

<210> SEQ ID NO 5
<211> LENGTH: 111
<212> TYPE: PRT
<213> ORGANISM: Artificial
<220> FEATURE:
<223> OTHER INFORMATION: Synthetic peptide

<400> SEQUENCE: 5

Gln Ser Val Leu Thr Gln Pro Pro Ser Val Ser Ala Ala Pro Gly Gln
1               5                   10                  15

Lys Val Thr Ile Ser Cys Ser Gly Ser Thr Ser Asn Ile Gly Asp Asn
            20                  25                  30

Tyr Val Ser Trp Tyr Gln Gln Leu Pro Gly Thr Ala Pro Gln Leu Leu
        35                  40                  45

Ile Tyr Asp Asn Thr Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu

```
                    85                  90                  95

Ser Gly Val Val Phe Gly Gly Gly Thr Lys Leu Thr Val Leu Gly
            100                 105                 110

<210> SEQ ID NO 6
<211> LENGTH: 109
<212> TYPE: PRT
<213> ORGANISM: Artificial
<220> FEATURE:
<223> OTHER INFORMATION: Synthetic peptide

<400> SEQUENCE: 6

Ser Tyr Val Leu Thr Gln Pro Pro Ser Val Ser Val Ala Pro Gly Gln
1               5                   10                  15

Thr Ala Thr Val Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Arg Arg Val Glu Ala Gly
65                  70                  75                  80

Asp Glu Ala Asp Tyr Tyr Cys Gln Val Trp Asp Ser Ser Asp His
                85                  90                  95

Asn Val Phe Gly Ser Gly Thr Lys Val Glu Ile Lys Arg
            100                 105

<210> SEQ ID NO 7
<211> LENGTH: 109
<212> TYPE: PRT
<213> ORGANISM: Artificial
<220> FEATURE:
<223> OTHER INFORMATION: Synthetic peptide

<400> SEQUENCE: 7

Leu Pro Val Leu Thr Gln Pro Pro Ser Val Ser Val Ala Pro Gly Gln
1               5                   10                  15

Thr Ala Arg Ile Ser Cys Gly Gly Asn Asn Ile Glu Thr Ile Ser Val
            20                  25                  30

His Trp Tyr Gln Gln Lys Pro Gly Gln Ala Pro Val Leu Val Val Ser
        35                  40                  45

Asp Asp Ser Val Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp Tyr
                85                  90                  95

Val Val Phe Gly Gly Gly Thr Lys Leu Thr Val Leu Gly
            100                 105

<210> SEQ ID NO 8
<211> LENGTH: 124
<212> TYPE: PRT
<213> ORGANISM: Artificial
<220> FEATURE:
<223> OTHER INFORMATION: Synthetic peptide

<400> SEQUENCE: 8

Gln Val Gln Leu Val Gln Ser Gly Ala Glu Val Lys Lys Pro Gly Ala
1               5                   10                  15
```

Ser Val Lys Val Ser Cys Thr Ala Ser Gly Tyr Ser Phe Thr Gly Tyr
            20                  25                  30

Phe Leu His Trp Val Arg Gln Ala Pro Gly Gln Gly Leu Glu Trp Met
            35                  40                  45

Gly Arg Ile Asn Pro Asp Ser Gly Asp Thr Ile Tyr Ala Gln Lys Phe
        50                  55                  60

Gln Asp Arg Val Thr Leu Thr Arg Asp Thr Ser Ile Gly Thr Val Tyr
65                  70                  75                  80

Met Glu Leu Thr Ser Leu Thr Ser Asp Thr Ala Val Tyr Tyr Cys
                85                  90                  95

Ala Arg Val Pro Arg Gly Thr Tyr Leu Asp Pro Trp Tyr Phe Asp
                100                 105                 110

Tyr Trp Gly Gln Gly Thr Leu Val Thr Val Ser Ser
            115                 120

<210> SEQ ID NO 9
<211> LENGTH: 124
<212> TYPE: PRT
<213> ORGANISM: Artificial
<220> FEATURE:
<223> OTHER INFORMATION: Synthetic peptide

<400> SEQUENCE: 9

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala His Val Leu Arg Phe Leu Glu Trp Leu Pro Asp Ala Phe Asp
                100                 105                 110

Ile Trp Gly Gln Gly Thr Leu Val Thr Val Ser Ser
            115                 120

<210> SEQ ID NO 10
<211> LENGTH: 119
<212> TYPE: PRT
<213> ORGANISM: Artificial
<220> FEATURE:
<223> OTHER INFORMATION: Synthetic peptide

<400> SEQUENCE: 10

Glu Val Gln Leu Val Glu Ser Gly Gly Gly Val Ala Gln Pro Gly Gly
1               5                   10                  15

Ser Leu Arg Val Ser Cys Ala Ala Ser Gly Phe Ser Phe Ser Ser Tyr
            20                  25                  30

Ala Met Gln Trp Val Arg Gln Ala Pro Gly Lys Gly Leu Glu Trp Val
            35                  40                  45

Ala Val Ile Ser Asn Asp Gly Arg Ile Glu His Tyr Ala Asp Ala Val
        50                  55                  60

Arg Gly Arg Phe Thr Ile Ser Arg Asp Asn Ser Gln Asn Thr Val Phe

```
                65                  70                  75                  80
Leu Gln Met Asn Ser Leu Arg Ser Asp Asp Thr Ala Leu Tyr Tyr Cys
                    85                  90                  95

Ala Arg Glu Ile Gly Ala Thr Gly Tyr Leu Asp Asn Trp Gly Gln Gly
                100                 105                 110

Thr Leu Val Thr Val Ser Ser
        115

<210> SEQ ID NO 11
<211> LENGTH: 122
<212> TYPE: PRT
<213> ORGANISM: Artificial
<220> FEATURE:
<223> OTHER INFORMATION: Synthetic peptide

<400> SEQUENCE: 11

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ala Gly Ile Ala Val Ala Gly Thr Cys Phe Asp Tyr Trp
            100                 105                 110

Gly Gln Gly Thr Leu Val Thr Val Ser Ser
        115                 120

<210> SEQ ID NO 12
<211> LENGTH: 245
<212> TYPE: PRT
<213> ORGANISM: Artificial
<220> FEATURE:
<223> OTHER INFORMATION: Synthetic peptide

<400> SEQUENCE: 12

Asp Ile Val Met Thr Gln Ser Pro Ser Ser Leu Ser Ala Ser Val Gly
1               5                   10                  15

Asp Arg Val Thr Leu Thr Cys Thr Ala Ser Gln Ser Val Ser Asn Asp
            20                  25                  30

Val Val Trp Tyr Gln Gln Arg Pro Gly Lys Ala Pro Lys Leu Leu Ile
        35                  40                  45

Tyr Ser Ala Phe Asn Arg Tyr Thr Gly Val Pro Ser Arg Phe Ser Gly
    50                  55                  60

Arg Gly Tyr Gly Thr Asp Phe Thr Leu Thr Ile Ser Ser Leu Gln Pro
65                  70                  75                  80

Glu Asp Val Ala Val Tyr Tyr Cys Gln Gln Asp Tyr Asn Ser Pro Arg
                85                  90                  95

Thr Phe Gly Gln Gly Thr Lys Leu Glu Val Lys Arg Gly Gly Gly Gly
            100                 105                 110

Ser Gly Gly Gly Gly Ser Gly Gly Gly Gly Ser Gly Gly Gly Gly Ser
        115                 120                 125
```

Gln Val Gln Leu Val Gln Ser Gly Ala Glu Val Lys Lys Pro Gly Ala
130                 135                 140

Ser Val Lys Val Ser Cys Thr Ala Ser Gly Tyr Thr Phe Thr His Tyr
145                 150                 155                 160

Gly Met Asn Trp Val Arg Gln Ala Pro Gly Lys Gly Leu Glu Trp Met
                165                 170                 175

Gly Trp Ile Asn Thr Tyr Thr Gly Glu Pro Thr Tyr Ala Asp Lys Phe
            180                 185                 190

Lys Asp Arg Phe Thr Phe Ser Leu Glu Thr Ser Ala Ser Thr Val Tyr
                195                 200                 205

Met Glu Leu Thr Ser Leu Thr Ser Asp Asp Thr Ala Val Tyr Tyr Cys
210                 215                 220

Ala Arg Glu Arg Gly Asp Ala Met Asp Tyr Trp Gly Gln Gly Thr Leu
225                 230                 235                 240

Val Thr Val Ser Ser
                245

<210> SEQ ID NO 13
<211> LENGTH: 245
<212> TYPE: PRT
<213> ORGANISM: Artificial
<220> FEATURE:
<223> OTHER INFORMATION: Synthetic peptide

<400> SEQUENCE: 13

Asp Ile Val Met Thr Gln Ser Pro Ser Ser Leu Ser Ala Ser Val Gly
1               5                   10                  15

Asp Arg Val Thr Leu Thr Cys Thr Ala Ser Gln Ser Val Ser Asn Asp
                20                  25                  30

Val Val Trp Tyr Gln Gln Arg Pro Gly Lys Ala Pro Lys Leu Leu Ile
            35                  40                  45

Tyr Ser Ala Phe Asn Arg Tyr Thr Gly Val Pro Ser Arg Phe Ser Gly
    50                  55                  60

Arg Gly Tyr Gly Thr Asp Phe Thr Leu Thr Ile Ser Ser Leu Gln Pro
65                  70                  75                  80

Glu Asp Val Ala Val Tyr Tyr Cys Gln Gln Asp Tyr Asn Ser Pro Arg
                85                  90                  95

Thr Phe Gly Gln Gly Thr Lys Leu Glu Val Lys Arg Gly Gly Gly Gly
            100                 105                 110

Ser Gly Gly Gly Gly Ser Gly Gly Gly Gly Ser Gly Gly Gly Gly Ser
        115                 120                 125

Gln Val Gln Leu Val Gln Ser Gly Ala Glu Val Lys Lys Pro Gly Ala
    130                 135                 140

Ser Val Lys Val Ser Cys Thr Ala Ser Gly Tyr Thr Phe Thr His Tyr
145                 150                 155                 160

Gly Met Asn Trp Val Arg Gln Ala Pro Gly Lys Gly Leu Glu Trp Met
                165                 170                 175

Gly Trp Ile Asn Thr Tyr Thr Gly Glu Pro Thr Tyr Ala Asp Lys Phe
            180                 185                 190

Lys Asp Arg Phe Thr Phe Ser Leu Glu Thr Ser Ala Ser Thr Val Tyr
        195                 200                 205

Met Glu Leu Thr Ser Leu Thr Ser Asp Asp Thr Ala Val Tyr Tyr Cys
    210                 215                 220

Ala Arg Glu Arg Gly Asp Ala Met Asp Tyr Trp Gly Gln Gly Thr Leu
225                 230                 235                 240

```
Val Thr Val Ser Ser
            245

<210> SEQ ID NO 14
<211> LENGTH: 245
<212> TYPE: PRT
<213> ORGANISM: Artificial
<220> FEATURE:
<223> OTHER INFORMATION: Synthetic peptide

<400> SEQUENCE: 14

Asp Ile Val Met Thr Gln Thr Pro Lys Phe Leu Leu Val Ser Ala Gly
 1               5                  10                  15

Asp Arg Val Thr Ile Thr Cys Thr Ala Ser Gln Ser Val Ser Asn Asp
            20                  25                  30

Val Val Trp Tyr Gln Gln Lys Pro Gly Gln Ser Pro Lys Met Leu Met
        35                  40                  45

Tyr Ser Ala Phe Asn Arg Tyr Thr Gly Val Pro Asp Arg Phe Thr Gly
 50                  55                  60

Arg Gly Tyr Gly Thr Asp Phe Thr Phe Thr Ile Ser Ser Val Gln Ala
 65                  70                  75                  80

Glu Asp Leu Ala Val Tyr Phe Cys Gln Gln Asp Tyr Asn Ser Pro Arg
                85                  90                  95

Thr Phe Gly Gly Gly Thr Lys Leu Glu Ile Lys Arg Gly Gly Gly Gly
            100                 105                 110

Ser Gly Gly Gly Gly Ser Gly Gly Gly Gly Ser Gly Gly Gly Gly Ser
        115                 120                 125

Gln Ile Gln Leu Val Gln Ser Gly Pro Glu Leu Lys Lys Pro Gly Glu
130                 135                 140

Thr Val Lys Ile Ser Cys Lys Ala Ser Gly Tyr Thr Phe Thr His Tyr
145                 150                 155                 160

Gly Met Asn Trp Val Lys Gln Ala Pro Gly Lys Gly Leu Lys Trp Met
                165                 170                 175

Gly Trp Ile Asn Thr Tyr Thr Gly Glu Pro Thr Tyr Ala Asp Asp Phe
            180                 185                 190

Lys Glu His Phe Ala Phe Ser Leu Glu Thr Ser Ala Ser Thr Val Phe
        195                 200                 205

Leu Gln Ile Asn Asn Leu Lys Asn Glu Asp Thr Ala Thr Tyr Phe Cys
210                 215                 220

Ala Arg Glu Arg Gly Asp Ala Met Asp Tyr Trp Gly Gln Gly Thr Ser
225                 230                 235                 240

Val Thr Val Ser Ser
            245

<210> SEQ ID NO 15
<211> LENGTH: 251
<212> TYPE: PRT
<213> ORGANISM: Artificial
<220> FEATURE:
<223> OTHER INFORMATION: Synthetic peptide

<400> SEQUENCE: 15

Asp Ile Gln Leu Thr Gln Ser Pro Ser Ser Leu Ser Ala Ser Val Gly
 1               5                  10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45
```

```
Tyr Phe Thr Ser Ser Leu His Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Ser Thr Val Pro Trp
                 85                  90                  95

Thr Phe Gly Gln Gly Thr Lys Val Glu Ile Lys Arg Gly Gly Gly Gly
            100                 105                 110

Ser Gly Gly Gly Gly Ser Gly Gly Gly Gly Ser Gly Gly Gly Gly Ser
        115                 120                 125

Glu Val Gln Leu Val Glu Ser Gly Gly Gly Leu Val Gln Pro Gly Gly
    130                 135                 140

Ser Leu Arg Leu Ser Cys Ala Ala Ser Gly Tyr Asp Phe Thr His Tyr
145                 150                 155                 160

Gly Met Asn Trp Val Arg Gln Ala Pro Gly Lys Gly Leu Glu Trp Val
                165                 170                 175

Gly Trp Ile Asn Thr Tyr Thr Gly Glu Pro Thr Tyr Ala Ala Asp Phe
            180                 185                 190

Lys Arg Arg Phe Thr Phe Ser Leu Asp Thr Ser Lys Ser Thr Ala Tyr
                195                 200                 205

Leu Gln Met Asn Ser Leu Arg Ala Glu Asp Thr Ala Val Tyr Tyr Cys
    210                 215                 220

Ala Lys Tyr Pro Tyr Tyr Tyr Thr Ser Ser His Trp Tyr Phe Asp Val
225                 230                 235                 240

Trp Gly Gln Gly Thr Leu Val Thr Val Ser Ser
                245                 250

<210> SEQ ID NO 16
<211> LENGTH: 20
<212> TYPE: PRT
<213> ORGANISM: Artificial
<220> FEATURE:
<223> OTHER INFORMATION: Synthetic peptide

<400> SEQUENCE: 16

Gly Gly Gly Gly Ser Gly Gly Gly Gly Ser Gly Gly Gly Gly Ser Gly
 1               5                  10                  15

Gly Gly Gly Ser
            20

<210> SEQ ID NO 17
<211> LENGTH: 20
<212> TYPE: PRT
<213> ORGANISM: Artificial
<220> FEATURE:
<223> OTHER INFORMATION: Synthetic peptide

<400> SEQUENCE: 17

Gly Gly Gly Gly Ser Gly Gly Gly Gly Ser Gly Gly Gly Gly Ser Ser
 1               5                  10                  15

Gly Gly Gly Ser
            20

<210> SEQ ID NO 18
<211> LENGTH: 245
<212> TYPE: PRT
<213> ORGANISM: Artificial
<220> FEATURE:
<223> OTHER INFORMATION: Synthetic peptide
```

<400> SEQUENCE: 18

```
Asp Ile Val Met Thr Gln Ser Pro Ser Ser Leu Ser Ala Ser Val Gly
1               5                   10                  15

Asp Arg Val Thr Leu Thr Cys Thr Ala Ser Gln Ser Val Ser Asn Asp
            20                  25                  30

Val Val Trp Tyr Gln Gln Arg Pro Gly Lys Ala Pro Lys Leu Leu Ile
        35                  40                  45

Tyr Ser Ala Phe Asn Arg Tyr Thr Gly Val Pro Ser Arg Phe Ser Gly
    50                  55                  60

Arg Gly Tyr Gly Thr Asp Phe Thr Leu Thr Ile Ser Ser Leu Gln Pro
65                  70                  75                  80

Glu Asp Val Ala Val Tyr Tyr Cys Gln Gln Asp Tyr Asn Ser Pro Arg
                85                  90                  95

Thr Phe Gly Gln Gly Thr Lys Leu Glu Val Lys Arg Gly Gly Gly Gly
            100                 105                 110

Ser Gly Gly Gly Gly Ser Gly Gly Gly Ser Ser Gly Gly Gly Gly Ser
        115                 120                 125

Gln Val Gln Leu Val Gln Ser Gly Ala Glu Val Lys Lys Pro Gly Ala
    130                 135                 140

Ser Val Lys Val Ser Cys Thr Ala Ser Gly Tyr Thr Phe Thr His Tyr
145                 150                 155                 160

Gly Met Asn Trp Val Arg Gln Ala Pro Gly Arg Gly Leu Glu Trp Met
                165                 170                 175

Gly Trp Ile Asn Thr Tyr Thr Gly Glu Pro Thr Tyr Ala Asp Lys Phe
            180                 185                 190

Lys Asp Arg Ile Thr Phe Ser Leu Glu Thr Ser Ala Ser Thr Val Tyr
        195                 200                 205

Met Glu Leu Thr Ser Leu Thr Ser Asp Asp Thr Ala Val Tyr Tyr Cys
    210                 215                 220

Ala Arg Glu Arg Gly Asp Ala Met Asp Tyr Trp Gly Gln Gly Thr Leu
225                 230                 235                 240

Val Thr Val Ser Ser
                245
```

<210> SEQ ID NO 19
<211> LENGTH: 245
<212> TYPE: PRT
<213> ORGANISM: Artificial
<220> FEATURE:
<223> OTHER INFORMATION: Synthetic peptide

<400> SEQUENCE: 19

```
Asp Ile Val Met Thr Gln Ser Pro Ser Ser Leu Ser Ala Ser Val Gly
1               5                   10                  15

Asp Arg Val Thr Leu Thr Cys Thr Ala Ser Gln Ser Val Ser Asn Asp
            20                  25                  30

Val Val Trp Tyr Gln Gln Arg Pro Gly Lys Ala Pro Lys Leu Leu Ile
        35                  40                  45

Tyr Ser Ala Phe Asn Arg Tyr Thr Gly Val Pro Ser Arg Phe Ser Gly
    50                  55                  60

Arg Gly Tyr Gly Thr Asp Phe Thr Leu Thr Ile Ser Ser Leu Gln Pro
65                  70                  75                  80

Glu Asp Val Ala Val Tyr Tyr Cys Gln Gln Asp Tyr Asn Ser Pro Arg
                85                  90                  95
```

Thr Phe Gly Gln Gly Thr Lys Leu Glu Val Lys Arg Gly Gly Gly
            100                 105                 110

Ser Gly Gly Gly Gly Ser Gly Gly Gly Ser Gly Gly Gly Ser
            115                 120                 125

Gln Val Gln Leu Val Gln Ser Gly Ala Glu Val Lys Lys Pro Gly Ala
            130                 135                 140

Ser Val Lys Val Ser Cys Thr Ala Ser Gly Tyr Thr Phe Thr His Tyr
145                 150                 155                 160

Gly Met Asn Trp Val Arg Gln Ala Pro Gly Lys Gly Leu Glu Trp Met
                165                 170                 175

Gly Trp Ile Asn Thr Tyr Thr Gly Glu Pro Thr Tyr Ala Asp Lys Phe
            180                 185                 190

Lys Asp Arg Ala Thr Phe Ser Leu Glu Thr Ser Ala Ser Thr Val Tyr
            195                 200                 205

Met Glu Leu Thr Ser Leu Thr Ser Asp Asp Thr Ala Val Tyr Tyr Cys
            210                 215                 220

Ala Arg Glu Arg Gly Asp Ala Met Asp Tyr Trp Gly Gln Gly Thr Leu
225                 230                 235                 240

Val Thr Val Ser Ser
            245

<210> SEQ ID NO 20
<211> LENGTH: 245
<212> TYPE: PRT
<213> ORGANISM: Artificial
<220> FEATURE:
<223> OTHER INFORMATION: Synthetic peptide

<400> SEQUENCE: 20

Asp Ile Val Met Thr Gln Ser Pro Ser Ser Leu Ser Ala Ser Val Gly
1               5                   10                  15

Asp Arg Val Thr Leu Thr Cys Thr Ala Ser Gln Ser Val Ser Asn Asp
            20                  25                  30

Val Val Trp Tyr Gln Gln Arg Pro Gly Lys Ala Pro Lys Leu Leu Ile
            35                  40                  45

Tyr Ser Ala Phe Asn Arg Tyr Thr Gly Val Pro Ser Arg Phe Ser Gly
50                  55                  60

Arg Gly Tyr Gly Thr Asp Phe Thr Leu Thr Ile Ser Ser Leu Gln Pro
65                  70                  75                  80

Glu Asp Val Ala Val Tyr Tyr Cys Gln Gln Asp Tyr Asn Ser Pro Arg
            85                  90                  95

Thr Phe Gly Gln Gly Thr Lys Leu Glu Val Lys Arg Gly Gly Gly Gly
            100                 105                 110

Ser Gly Gly Gly Gly Ser Gly Gly Gly Ser Gly Gly Gly Ser
            115                 120                 125

Gln Val Gln Leu Val Gln Ser Gly Ala Glu Val Lys Lys Pro Gly Ala
            130                 135                 140

Ser Val Lys Val Ser Cys Thr Ala Ser Gly Tyr Thr Phe Thr His Tyr
145                 150                 155                 160

Gly Met Asn Trp Val Arg Gln Ala Pro Gly Lys Gly Leu Glu Trp Met
                165                 170                 175

Gly Trp Ile Asn Thr Tyr Thr Gly Glu Pro Thr Tyr Ala Asp Lys Phe
            180                 185                 190

Lys Asp Arg Val Thr Leu Ser Leu Glu Thr Ser Ala Ser Thr Val Tyr
            195                 200                 205

```
Met Glu Leu Thr Ser Leu Thr Ser Asp Asp Thr Ala Val Tyr Tyr Cys
    210                 215                 220

Ala Arg Glu Arg Gly Asp Ala Met Asp Tyr Trp Gly Gln Gly Thr Leu
225                 230                 235                 240

Val Thr Val Ser Ser
                245

<210> SEQ ID NO 21
<211> LENGTH: 245
<212> TYPE: PRT
<213> ORGANISM: Artificial
<220> FEATURE:
<223> OTHER INFORMATION: Synthetic peptide

<400> SEQUENCE: 21

Asp Ile Val Met Thr Gln Ser Pro Ser Ser Leu Ser Ala Ser Val Gly
1               5                   10                  15

Asp Arg Val Thr Leu Thr Cys Thr Ala Ser Gln Ser Val Ser Asn Asp
                20                  25                  30

Val Val Trp Tyr Gln Gln Arg Pro Gly Lys Ala Pro Lys Leu Leu Ile
            35                  40                  45

Tyr Ser Ala Phe Asn Arg Tyr Thr Gly Val Pro Ser Arg Phe Ser Gly
    50                  55                  60

Arg Gly Tyr Gly Thr Asp Phe Thr Leu Thr Ile Ser Ser Leu Gln Pro
65                  70                  75                  80

Glu Asp Val Ala Val Tyr Tyr Cys Gln Gln Asp Tyr Asn Ser Pro Arg
                85                  90                  95

Thr Phe Gly Gln Gly Thr Lys Leu Glu Val Lys Arg Gly Gly Gly Gly
            100                 105                 110

Ser Gly Gly Gly Gly Ser Gly Gly Gly Ser Ser Gly Gly Gly Ser
            115                 120                 125

Gln Val Gln Leu Val Gln Ser Gly Ala Glu Val Lys Lys Pro Gly Ala
    130                 135                 140

Ser Val Lys Val Ser Cys Thr Ala Ser Gly Tyr Thr Phe Thr His Tyr
145                 150                 155                 160

Gly Met Asn Trp Val Arg Gln Ala Pro Gly Lys Gly Leu Glu Trp Met
                165                 170                 175

Gly Trp Ile Asn Thr Tyr Thr Gly Glu Pro Thr Tyr Ala Asp Lys Phe
            180                 185                 190

Lys Asp Arg Phe Thr Leu Ser Leu Glu Thr Ser Ala Ser Thr Val Tyr
        195                 200                 205

Met Glu Leu Thr Ser Leu Thr Ser Asp Asp Thr Ala Val Tyr Tyr Cys
    210                 215                 220

Ala Arg Glu Arg Gly Asp Ala Met Asp Tyr Trp Gly Gln Gly Thr Leu
225                 230                 235                 240

Val Thr Val Ser Ser
                245

<210> SEQ ID NO 22
<211> LENGTH: 5
<212> TYPE: PRT
<213> ORGANISM: Artificial
<220> FEATURE:
<223> OTHER INFORMATION: Synthetic peptide
```

```
<400> SEQUENCE: 22

Gly Gly Gly Gly Ser
1               5
```

SCFV ANTIBODIES WHICH PASS EPITHELIAL AND/OR ENDOTHELIAL LAYERS

FIELD OF THE INVENTION

The present invention concerns an scFv antibody with improved features for tissue penetration and its topical application in the diagnosis and treatment of a disease dependent on the over-expression of a selected antigen. In particular, the invention concerns an antibody which specifically binds and inactivates said selected antigen.

RELATED INFORMATION

The contents of any patents, patent applications, and references cited throughout this specification are hereby incorporated by reference in their entireties.

BACKGROUND OF THE INVENTION

Local treatment of many diseases can occur by topical application of a drug that must be able to penetrate epithelial tissue. Adjacent epithelial cells are sealed by tight junctions, preventing the passage of most dissolved molecules from one side of the epithelial sheet to the other (Alberts et al., Molecular Biology of the Cell, 2nd ed.). Tight junctions are crucial for the formation and maintenance of the paracellular barrier and for cell polarity in simple epithelia and endothelia. They also play an important role at the blood brain barrier, where they control substances that leave or enter the brain. Large molecular weight drugs need to pass through these tissue barriers in order to get to their sites of action. In general, antibodies are too big to cross the tight junctions of epithelial cell layers.

As part of the body's normal activity, tight junctions selectively open and close in response to various signals both inside and outside of cells. This allows the passage of large molecules or even entire cells to across the tight junction barrier.

Mucosal administration of therapeutic compounds may offer certain advantages over injection and other modes of administration, for example in terms of convenience and speed of delivery, as well as by reducing or eliminating compliance problems and side effects that attend delivery by injection. However, mucosal delivery of biologically active agents is limited by mucosal barrier functions and other factors. For these reasons, mucosal drug administration typically requires larger amounts of drug than administration by injection. Other therapeutic compounds, including large molecule drugs, peptides and proteins, are often refractory to mucosal delivery.

The ability of drugs to permeate mucosal surfaces, unassisted by delivery-enhancing agents, appears to be related to a number of factors, including molecular size, lipid solubility, and ionization. Small molecules, less than about 300-1,000 daltons, are often capable of penetrating mucosal barriers, however, as molecular size increases, permeability decreases rapidly. Lipid-soluble compounds are generally more permeable through mucosal surfaces than are non-lipid-soluble molecules. Peptides and proteins are poorly lipid soluble, and hence exhibit poor absorption characteristics across mucosal surfaces.

US2006062758 provides compositions and methods that include a biologically active agent and a permeabilizing peptide effective to enhance mucosal delivery of the biologically active agent in a mammalian subject. The permeabilizing peptide reversibly enhances mucosal epithelial paracellular transport, typically by modulating epithelial junctional structure and/or physiology at a mucosal epithelial surface in the subject.

Peptides capable of modulating the function of epithelial tight junctions have been previously described (Johnson, P. H. and Quay, S. C., 2000). CA2379661 provides a paracellular drug delivery system comprising a Caludin-6 derived peptide. Claudins represent a super-family of integral membrane proteins located at the tight junctions and providing the barrier function.

Antibodies are powerful tools for biochemical and molecular biology research and are widely applied in medical diagnostics and therapy due to their ability to specifically bind to their antigen with high affinity. Typically, antibodies consist of two heavy and two light chains, which are covalently linked to each other via disulfide bonds. A highly variable domain comprising three complementary regions (CDRs) is positioned at the N-terminus of each chain. In concert, variable regions of the heavy and light chain determine antigen specificity of the antibody. Single chain antibodies (scFv) have been engineered by linking the DNA sequences encoding variable heavy (VH) and variable light (VL) domains with a spacer sequence coding for a flexible amino acid linker (Bird et al., 1988).

This format has the advantages over conventional full-length antibodies that an scFv is encoded by a single gene, mutations can be easily introduced, and the resulting scFv can be expressed in yeast and prokaryotic systems, which allow for rapid selection of specific high affinity binders to virtually any epitope by simple molecular biology. Due to their lack of effector function, scFv antibodies do not exert toxic effects via antibody-dependent or complement-dependent cell-mediated cytotoxicity (ADCC or CDCC, respectively), and unlike full-length antibodies, scFv antibodies show good tissue penetration abilities.

Many single chain antibodies (scFvs) have been generated against a multitude of different antigens, in particular because they can be easily selected for high binding capacity using techniques such as phage display or ribosome display. Moreover, scFv antibodies can be produced in microbial systems which are associated with fewer costs compared to the production of therapeutic full-length antibodies.

In addition to conventional extracellular and in vitro applications, scFvs have also been successfully used for intracellular applications (Worn et al. 2000; Auf der Maur et al. 2002; Stocks M R, 2004); hence, scFvs directed against intracellular antigens have been developed. In general, intracellular expression of functional scFvs is limited by their instability, insolubility, and tendency to form aggregates. For this reason, in vivo screening systems for scFv antibodies, which are particularly soluble and stable under reducing conditions typical for the intracellular environment (e.g. nucleus, cytoplasm) have been successfully developed using a so called "Quality Control" screen (WO0148017; Auf der Maur et al. (2001); Auf der Maur et al., 2004) and have led to the identification of particularly stable and soluble scFv framework sequences for such purposes (WO03097697). Furthermore, these frameworks show exceptional expression levels and enhanced stability and solubility properties also under natural, oxidizing conditions in the extracellular environment. Hence, these favourable biophysical and biochemical properties translate into favourable high production yields and enable these antibody fragments, once directed against specific antigens, to be applied locally and/or systemically as protein therapeutics in particular therapeutic areas.

For the use of antibodies in many therapeutic applications, in particular local applications, an important factor is the ability of the antibody to penetrate tissues, and in particular epithelial tissue barriers.

Local application is particularly desirable for the treatment of disorders that are manifested at a particular locus and do not require a systemic treatment, for example eye diseases.

Uveitis Anterior

Uveitis is an acute or chronic inflammation of the uvea with a prevalence of 30-40 per 100,000 (Lightman and Kok 2002). Uveitis is subdivided by location in uveitis anterior, intermediate or posterior. Uveitis anterior develops into uveitis posterior followed by complications such as cataracts, retinitis and even blindness, if left untreated (Kok and Lightman 2004). In <65 year olds there are as many legally blind individuals as a result from uveitis as diabetic retinopathy (Kok and Lightman 2004). Uveitis anterior, as the most common form of intra-ocular inflammatory diseases, is associated with histocompatibility locus A allele B27 (HLA-B27) in 50% of the cases (Power et al. 1998). Of these patients, only about half suffer from an additional systemic disease such as ankylosing spondylitis or chronic inflammatory bowel disease (El-Shabrawi and Hermann 2002). The treatment of uveitis is primarily aimed at controlling the inflammatory process (Kok and Lightman 2004). Currently, corticosteroids are the mainstay for therapy of uveitis (Kok and Lightman 2004). Importantly, local and systemic corticosteroid treatment significantly increases the risk of glaucoma and cataract, thus limiting its repeated use (El-Shabrawi and Hermann 2002). Other treatments including methotrexate, cyclosporine or azathioprine require a minimum of 6 weeks treatment to produce an effect, leaving patients with an enormous constraint of quality of life for a long period (El-Shabrawi and Hermann 2002, Dick et al. 1997).

From the above, a clearly defined medical need is obvious. Topical corticosteroids as the most common therapeutic option have significant side-effects, which in fact exacerbate the long term risk of blindness.

Recently TNFα concentrations of 15 pg/ml have been found in aqueous humor of uveitis patients, whereas the corresponding levels in healthy individuals were 0.56 pg/ml (Perez-Guijo et al. 2004). Several small clinical studies performed with systemically applied TNFα inhibitors report "immediate improvement" (El-Shabrawi and Hermann 2002) or "marked clinical improvement within days" (Murphy et al. 2004) or "within 2 weeks" (Joseph 2003) or "significant improvement after the first infliximab dose" (Benitez Del Castillo et al. 2004).

Thus, the concept of targeting TNFα is clinically well validated. However, safety concerns related to systemic application of TNFα inhibitors remain and would not justify their use in the significant fraction of uveitis patients who lack additional systemic disease manifestations.

Therefore, a topical TNFα inhibitor will fill a well-defined medical need, especially in patients with uveitis anterior. Due to their large molecular weight, the marketed TNFα inhibitors are not applicable topically (see Thiel et al. 2002).

Behçet's Disease

Behçet's disease is an idiopathic, multisystemic, chronic, and recurrent disease, classically characterized by episodic aggressive ocular inflammatory attacks, orogenital ulcers and skin lesions. In rare, severe cases of Behçet's disease, articular, audio-vestibular, thoracic gastrointestinal, cardiovascular, renal or CNS involvement may be observed in addition. The eye is the most commonly involved internal organ in Behçet's disease and is the leading cause of chronic morbidity in patients. Ocular disease consists of unilateral (20%) or bilateral (80%) iridocyclitis, hypopyon or panuveitis running a chronic and relapsing course. In general, initial exacerbations tend to be more anterior and unilateral, whereas subsequent attacks tend to involve vitreal cavity and posterior segment of the eye, becoming bilateral (Evereklioglu 2005). Severe uveitis is more commonly observed among patients form endemic regions such as Japanese and Turkish patients, affecting 70-90% of this population (Özen 1999; Tursen et al., 2003; Tugal-Tutkun et al., 2004; Yurdakul et al., 2004; Evereklioglu 2005). The risk of visual loss increases progressively, reaching one-fourth of the cases at 10 years. In addition, legal blindness is significant and eventually ensues in more than 50% of cases in countries with high prevalence and severity of the disease, such as Japan (Boyd et al., 2001; Evereklioglu 2005).

Behçet's disease exhibits a distinct geographic variation and is endemically higher particularly in Japan, Korea, Saudi-Arabia, Iran and Turkey as well as in the countries along the ancient "silk road", including China and Israel (Bonfioli and Orefice 2005; Evereklioglu 2005). For example, Behçet's disease accounts for 20% of cases of uveitis in Japan and Turkey when compared with only 0.2% in the USA. In countries where the disease is endemic, it is more severe, with a higher frequency of ocular manifestations and complications and is more common in men, especially young male adults (Evereklioglu 2005). This peculiar epidemiology appears to be mediated by a combination of genetics (such as association with the HLA-B51 allele (Sakane et al., 1999; Verity et al., 1999; Evereklioglu 2005), infectious agents (Direskeneli 2001; Evereklioglu 2005) and environmental factors. The estimated prevalence of Behçet's disease is between 1:10,000 and 1:1000 in the Mediterranean countries, the Middle East, and the Far East. In Japan and Asian countries along the silk road, the prevalence is 13-30 per 100,000 and is highest in the northern parts of Japan; the highest overall prevalence with up to 400 per 100,000 is observed in certain parts of Turkey. There are approximately 15,000 people with Behçet's disease in the USA (Zierhut et al., 2003; Evereklioglu 2005).

Consequences of ophthalmic inflammatory attacks are the leading cause of chronic morbidity in Behçet's disease patients (Evereklioglu 2005). Treatment of Behçet's disease is symptomatic and empirical. As in other forms of uveitis, topical, periocular and systemic corticosteroids represent the mainstay of therapy in ocular Behçet's disease. However, the use of corticosteroid-based treatment modalities in the patients is limited by their significant side-effect profile. In addition, corticosteroids rarely induce complete remissions in ocular Behçet's disease and a significant fraction of patients develops steroid-resistant disease over time (Evereklioglu 2005). In the course of the disease, treatments frequently comprise immunosuppressive agents such as azathioprine, methotrexate and cyclosporine A. However, as these agents are associated with critical safety issues as well, there is a well-expressed medical need for an efficient and safe novel treatment modality in this indication.

Besides recent epidemiological findings that suggest polymorphic variations in TNFα to be associated with the severity of Behçet's disease (Verity et al., 1999b), there exists a broad variety of case reports and small clinical trials describing the use of infliximab in ocular Behçet's disease (Ohno et al., 2004; Wechsler et al., 2004; Giansanti et al., 2004; Lanthier et al., 2005; Tugal-Tutkun et al., 2005; Lindstedt et al., 2005). In fact, all these studies report rapid and complete remission of ocular Behçet's disease, even in patients resistant to conventional therapy (Tugal-Tutkun et al., 2005). However, the frequency and severity of adverse events in infliximab-treated uveitis patients is unexpectedly high in some studies, thus limiting the potential of systemically applied TNFα antagonists for treatment of this disease (Rosenbaum 2004; Suhler et al., 2005).

The clinical validation of TNFα as a highly attractive drug target in ocular Behçet's disease (Ohno et al., 2004; Wechsler et al., 2004; Giansanti et al., 2004; Lanthier et al., 2005; Tugal-Tutkun et al., 2005; Lindstedt et al., 2005) and the apparent safety concerns with systemic TNFα suppression in uveitis patients (Rosenbaum 2004; Suhler et al., 2005), reveals that there is a need for the development of a topically applicable TNFα antagonist for ocular Behçet's disease, especially for patients with predominant ocular symptoms.

Due to their good tissue penetration abilities and their rapid renal clearance, scFv antibodies are preferred for local applications. Besides charge, hydropathicity and molecular weight, properties such as solubility, aggregation tendency and thermal stability influence the ability of a molecule to penetrate through tissue barriers. For example, a highly soluble antibody fragment may not be able to penetrate epithelial barriers if it forms aggregates at physiological temperature around 37° C. Mutation of a single amino acid residue in an scFv framework may on the one hand improve its solubility at ambient temperature, and this mutation may alter thermal stability and therefore lead to partial unfolding and aggregation at 37° C. Such aggregates, due to their higher molecular weight, are no longer able to pass tissue barriers.

Because tissue penetration is an important factor for efficient drug delivery, in particular in local applications, there is a need for therapeutic antibodies, in particular scFv antibodies with improved tissue penetration abilities besides the otherwise desirable characteristics of high stability and low antigenicity. WO0040262 discloses antibody fragments, e.g. scFvs, as pharmaceuticals or diagnostic tools to treat or diagnose, respectively, ocular disorders. Eye penetration experiments are done at concentrations of 0.2 to 0.25 mg/ml scFv. It was shown that an scFv could penetrate the epithelial barrier of the cornea at a very low rate in the absence, and at higher rates in the presence of penetration enhancers. Since penetration enhancers can have cytotoxic effects or cause epithelial alterations, there is a need for alternative and/or improved methods for the treatment of ocular diseases by scFvs and fragments thereof. In particular, antibodies are needed for controlled therapy by local administration with a low degree of side effects, which can be administered at a relatively high concentration.

All publications and references cited herein are hereby incorporated by reference in their entirety.

SUMMARY OF THE INVENTION

Hence, it is a general object of the invention to provide an antibody, preferably an scFv antibody, which specifically binds a selected antigen and has improved tissue penetration ability.

Now, in order to implement these and still further objects of the invention, which will become more readily apparent as the description proceeds, said antibody is manifested by the feature that it is obtainable by a method comprising (i) selecting from a pool of soluble and stable frameworks the framework matching best to the framework of a non-human antibody of a selected antigen-binding specificity, (ii) either providing said framework with CDRs that bind said antigen or mutating the framework of said non-human antibody towards the sequence of said soluble and stable framework, (iii) testing the generated antibody for solubility and stability, and (iv) testing the generated antibody for antigen binding.

Optionally, between steps (ii) and (iii) the following step is added:

mutating said scFv antibody by site-directed or random mutagenesis of one or more selected CDRs and/or the framework.

The invention also provides a composition comprising a soluble antigen-binding polypeptide, wherein the antigen-binding polypeptide is capable of crossing one or more epithelial layers, for example, an endothelial layer or mesothelial layer, in less than about 8 hours. For example, the antigen-binding polypeptide is capable of crossing one or more epithelial layers in less than about 8, 7, 6, 5, 4, 3, 2, 1, or fewer hours. In one embodiment, the antigen-binding polypeptide is capable of crossing an epithelial layer or layers in less than about 4 hours. It is to be understood that all values and ranges between these values and ranges are meant to be encompassed by the present invention.

In other embodiments, the epithelial layer is of the eye, for example, of the cornea, for example the epithelium and/or endothelium of the cornea. In one embodiment, the epithelial layer is of the intestine. In yet another embodiment, the epithelial layer is the blood brain barrier.

In yet other embodiments, the antigen-binding polypeptide is capable of crossing an intact mammalian cornea in less than about 8 hours. For example, the antigen-binding polypeptide is capable of crossing an intact mammalian cornea in less than about 8, 7, 6, 5, 4, 3, 2, 1 or fewer hours. In one embodiment, the antigen-binding polypeptide is capable of crossing an intact human cornea. In one embodiment, the antigen-binding polypeptide is capable of crossing an intact pig or rabbit cornea.

In still other embodiments, the composition further comprises a penetration enhancer. In certain embodiments, the penetration enhancer is selected from the group consisting of Azone®, benzalkonium chloride (BzCl), BL-7, BL-9, Brij 35, Brij 78, Brij 98, Brij 99, Polyoxyethylene-Polyoxypropylene 1800, sodium caprate, caprylic acid, cetylpyridinium chloride, chlorhexidine, cholate, castor oil, corn oil, cremophor-EL, cyclodextrins, DMSO, decamethonium bromide, deoxycholate, dextransulfate, EDTA, disodium EDETATE, ethanol, fusidate, glycocholate, lauryl sulfate, L-α-lysophosphatidylocholine, methazolamide, N-lauroylsarcosine, NMP, oleic acid, Pz-peptide, phospholipids, poly oxyethylene-9-lauryl ether, saponin, Tween 20, Tween 40, Tween 60, Tween 80, taurocholeate, and taurodeoxycholate. In another embodiment, the penetration enhancer is sodium caprate. In yet another embodiment, the penetration enhancer includes colloidal systems, polyacrylates and bio-adhesive polymer.

In a preferred embodiment, the molecules of the invention can cross an epithelial layer, for example, an epithelial layer of the eye (cornea) in the absence of a penetration enhancer.

In some embodiments, the polypeptide has a binding affinity for a target antigen of a kD of at least 10E-6 M or better.

In some aspects, the present invention provides a composition having a pH of less than about 8, said composition comprising an antigen-binding polypeptide (e.g., single-chain antibody) wherein the polypeptide is sufficiently soluble to transit an intact cornea. In some embodiments, the composition has a pH in the range of about 6 to about 8. In other embodiments, the composition has a pH of about 6, 6.5, 7.0, 7.5, 8.0 or any incremental value thereof. It is understood that any values and ranges between these values and ranges are meant to be encompassed by the present invention.

In some aspects, the present invention provides a composition having a pH of less than about 8, said compositions comprising an antigen-binding polypeptide (e.g., single-chain antibody) wherein the polypeptide is sufficiently soluble to transit an intact cornea. In some aspects, the present invention provides a composition comprising a soluble antigen-binding polypeptide, and wherein the polypeptide is sufficiently soluble to transit an intact cornea in less than about 8 hours, and formulated at about pH 8 or less. In some embodiments, the polypeptide is sufficiently soluble to transit an intact cornea in less than about 4 hours. In other embodiments, the composition further comprises a penetration enhancing agent. In some embodiments, the penetration enhancing agent is selected from the group consisting of azone, benzalkonium chloride (BzCl), BL-7, BL-9, Brij 35, Brij 78, Brij 98, Brij 99, Polyoxyethylene-Polyoxypropylene 1800, sodium caprate, caprylic acid, cetylpyridinium chloride, chlorhexidine, cholate, castor oil, corn oil, cremophor-EL, DMSO, decamethonium bromide, deoxycholate, dextransulfate, EDTA, disodium EDETATE, ethanol, fusidate, glycocholate, lauryl sulfate, L-α-lysophosphatidylocholine, N-lauroylsarcosine, NMP, oleic acid, phospholipids, poly oxyethylene-9-lauryl ether, saponin, Tween 20, Tween 40, Tween 60, Tween 80, taurocholate, and taurodeoxycholate. In some embodiments, the penetration enhancing agent is sodium caprate. In some embodiments, the penetration enhancing agent is chlorhexidine.

In some aspects, the present invention provides a composition comprising a soluble antigen-binding polypeptide, wherein the antigen-binding polypeptide is capable of crossing one or more layers of an intact cornea in less than about 8 hours. In other aspects, the present invention provides a composition comprising an antigen-binding polypeptide (e.g., single-chain antibody) at a concentration of greater than about 2.5 mg/ml, wherein the polypeptide is sufficiently soluble to transit an intact cornea in less than about 8 hours. The composition can comprise an antigen-binding polypeptide at a concentration in the range of from greater than about 2.5 mg/ml to greater than about 10.0 mg/ml. For example, the composition can comprise an antigen-binding polypeptide at a concentration of about 2.5 mg/ml, 3.0 mg/ml, 3.5 mg/ml, 4.0 mg/ml, 4.5 mg/ml, 5.0 mg/ml, 5.5 mg/ml, 6.0 mg/ml, 6.5 mg/ml, 7.0 mg/ml, 7.5 mg/ml, 8.0 mg/ml, 8.5 mg/ml, 9.0 mg/ml, 9.5 mg/ml, to greater than about 10.0 mg/ml, or any incremental value thereof. It is to be understood that all values and ranges between these values and ranges are meant to be encompassed by the present invention. In some embodiments, the antigen-binding polypeptide is at a concentration of greater than about 4.0 mg/ml. In other embodiments, the antigen-binding polypeptide is at a concentration of greater than about 10.0 mg/ml.

In yet other embodiments, the polypeptide is sufficiently soluble to transit an intact cornea in less than about 4 hours. In other embodiments, the composition further comprises a penetration enhancing agent. In some embodiments, the penetration enhancing agent is selected from the group consisting of azone, benzalkonium chloride (BzCl), BL-7, BL-9, Brij 35, Brij 78, Brij 98, Brij 99, Polyoxyethylene-Polyoxypropylene 1800, sodium caprate, caprylic acid, cetylpyridinium chloride, chlorhexidine, cholate, castor oil, corn oil, cremophor-EL, DMSO, decamethonium bromide, deoxycholate, dextransulfate, EDTA, disodium EDETATE, ethanol, fusidate, glycocholate, lauryl sulfate, L-α-lysophosphatidylocholine, N-lauroylsarcosine, NMP, oleic acid, phospholipids, poly oxyethylene-9-lauryl ether, saponin, Tween 20, Tween 40, Tween 60, Tween 80, taurocholate, and taurodeoxycholate. In some embodiments, the penetration enhancing agent is sodium caprate. In other embodiments, the penetration enhancing agent is chlorhexidine.

In some aspects, the present invention provides an antigen-binding polypeptide (e.g., single-chain antibody), having a binding affinity for a target antigen of a kD of at least 10E-6 M and wherein the polypeptide is sufficiently soluble to transit an epithelial tight junction, and wherein the polypeptide remains in monomeric form under physiological conditions.

In other aspects, the present invention comprises a composition comprising an antigen-binding polypeptide wherein the antigen-binding polypeptide is stable at a temperature from about −80 degrees Celsius to about 37 degrees Celsius. For example, the composition may be stable at a temperature of −80 degrees Celsius, −70 degrees Celsius, −60 degrees Celsius, −50 degrees Celsius, −40 degrees Celsius, −30 degrees Celsius, −20 degrees Celsius, −10 degrees Celsius, 0 degrees Celsius, 10 degrees Celsius, 20 degrees Celsius, or 30 degrees Celsius, or any incremental value thereof. It is to be understood that all values and ranges between these values and ranges are meant to be encompassed by the present invention. In some embodiments, the antigen-binding polypeptide remains stable for at least about eight weeks. In other embodiments, the antigen-binding polypeptide remains stable for at least six weeks at 4 degrees Celsius.

In some aspects, the present invention provides a composition comprising an antigen-binding polypeptide, wherein the antigen-binding polypeptide has the pharmacodynamic or pharmacokinetic features as experimentally shown throughout any of the figures disclosed herein.

In other aspects, the present invention provides an antigen-binding polypeptide having a binding affinity for a target antigen of a kD of at least 10E-6 M or better and wherein the polypeptide is sufficiently soluble to transit an epithelial tight junction in less than about 8 hours. In some embodiments, the polypeptide is sufficiently soluble to transit an epithelial tight junction in about 4 hours or less.

In still yet other aspects, the present invention provides an antigen-binding polypeptide having a binding affinity for a target antigen of a kD of at least 10E-6 M or better and wherein the polypeptide has a ½ Vmax value corresponding to the transit kinetics of an antigen-binding polypeptide that can cross an epithelial tight junction in less than about 8 hours.

In other aspects, the present invention includes an antigen-binding polypeptide sufficiently soluble to transit an epithelial tight junction as measured in a standard Caco-2 (human colon adenocarcinoma) epithelial cell monolayer assay, as to be suitable for use in therapy. In various aspects, the present invention includes an antigen-binding polypeptide sufficiently soluble to transit an epithelial tight junction as measured in a standard mouse jejunum permeability assay, as to be suitable for use in therapy. In yet other aspects, the present invention includes an antigen-binding polypeptide sufficiently soluble to transit an epithelial tight junction as predicted by a standard intracellular one hybrid or two hybrid solubility assays, as to be suitable for use in therapy. In still yet other aspects, the present invention provides an antigen-binding polypeptide sufficiently soluble to transit an epithelial tight junction as predicted by a standard PEG precipitation assay or self-interaction chromatography (SIC) assay, as to be suitable for use in therapy.

In other aspects the present invention provides a method for identifying an antigen-binding polypeptide having a ½ Vmax value corresponding to transit of the antigen-binding polypeptide across an epithelial tight junction in less than about 8 hours. The method comprises: expressing intracellularly candidate antigen-binding polypeptides in host cells having an inducible reporter gene system, wherein the reporter gene system yields a recordable signal when in the presence of an antigen-binding polypeptide having said transit kinetics; and screening said cells for a recordable signal, wherein the presence of said signal identifies a candidate polypeptide as an antigen-binding polypeptide having said transit kinetics. The present invention, in some aspects, also provides for am antigen-binding polypeptide identified by this method. In some aspects, the present invention also provides a kit for carrying out this method.

In other aspects, the present invention provides a method of treating a patient with an ocular condition by topically administering a therapeutically effective amount of an antigen-binding polypeptide of any one of the claims herein, such that treatment is achieved. In some embodiments, the ocular condition is uveitis. In other embodiments, the ocular condition is age related macular degeneration.

In some aspects, the present invention provides an antigen-binding polypeptide comprising a polypeptide region having at least one antigen-binding motif flanked by at least one scaffold region and wherein the polypeptide has transit kinetics sufficient to cross an epithelial tight junction in less than about 8 hours. In some embodiments, the polypeptide comprises one antigen-binding motif flanked by two scaffold regions, two antigen-binding motifs flanked by three scaffold regions, three antigen-binding motifs flanked by four scaffold regions, or six antigen-binding motifs flanked by eight scaffold regions with an intervening linker region between the fourth and fifth scaffold regions. In other embodiments, the antigen-binding motif is a CDR and the scaffold region is an immunoglobulin framework region. In still yet other embodiments, the polypeptide comprises three CDRs and four intervening framework regions or six CDRs and eight framework regions and an intervening linker region.

In some aspects, the present invention also provides an antigen-binding polypeptide capable of specifically binding a target antigen and having transit kinetics sufficient to cross an epithelial tight junction in less than about 8 hours and wherein the polypeptide is represented by the formula:

Y; or

Z; or

Y-L-Z; or

Z-L-Y;

with Y being [F1-CDR1-F2-CDR2-F3-CDR3 F4] and Z being [F5-CDR1-F6-CDR2-F7-CDR3 F8];

wherein the framework regions (F1-F4) of Y are derived from one or more human light chain frameworks; the framework regions (F5-F6) of Z are derived from one or more human light chain frameworks; the CDRs (CDRs1-3) of Y are derived from one or more donor CDRs capable of binding the target antigen; the CDRs (CDRs4-6) of Z are derived from one or more donor CDRs capable of binding the target antigen; and L is a flexible polypeptide linker. In some embodiments, Y and Z are represented by any of the sequences disclosed herein, or consensus thereof.

Alternatively, in another embodiment, mutations can be are randomly introduced randomly along all or part of the antigen-binding polypeptide coding sequence, such as by saturation mutagenesis. A "consensus sequence" is a sequence formed from the most frequently occurring amino acids (or nucleotides) in a family of related sequences (See e.g., Winnaker, From Genes to Clones (Verlagsgesellschaft, Weinheim, Germany 1987). In a family of proteins, each position in the consensus sequence is occupied by the amino acid occurring most frequently at that position in the family. If two amino acids occur equally frequently, either can be included in the consensus sequence.

In some aspects, the present invention provides an antigen-binding polypeptide formulated to achieve an intraocular concentration of at least about 100 ng/ml or more. In yet other aspects, the present invention provides a single chain antibody formulated for topical administration to yield an intraocular concentration of 100 ng/ml or more based on a cellular or animal model system as disclosed herein.

In other aspects, the present invention provides an antigen-binding polypeptide formulated for topical application to eye and capable of passing through the cornea and into an intraocular space in the absence of penetration enhancer. In yet other aspects, the present invention provides a method for treating, preventing or diagnosing an eye disease or disorder using a polypeptide of any one of the claims.

BRIEF DESCRIPTION OF THE DRAWINGS

The foregoing and other aspects, embodiments, objects, features and advantages of the invention can be more fully understood from the following description in conjunction with the accompanying drawings. In the drawings like reference characters generally refer to like features and structural elements throughout the various figures. The drawings are not necessarily to scale, emphasis instead being placed upon illustrating the principles of the invention.

FIG. 11a is a graphical depiction of the amount of ESBA105 in ng/ml found in the aqueous humour of the rabbit eyes sampled over the course of the study described in Example 7.

FIG. 11b is a graphical depiction of the amount of ESBA105 in ng/ml found in the vitreous humour of the rabbit eyes sampled over the course of the study described in Example 7.

FIG. 17 shows dose response data in a relevant in vivo acute monoarthritis (rat) model. n=3, TNFα: 10 µg i.a.

Figure 1A:
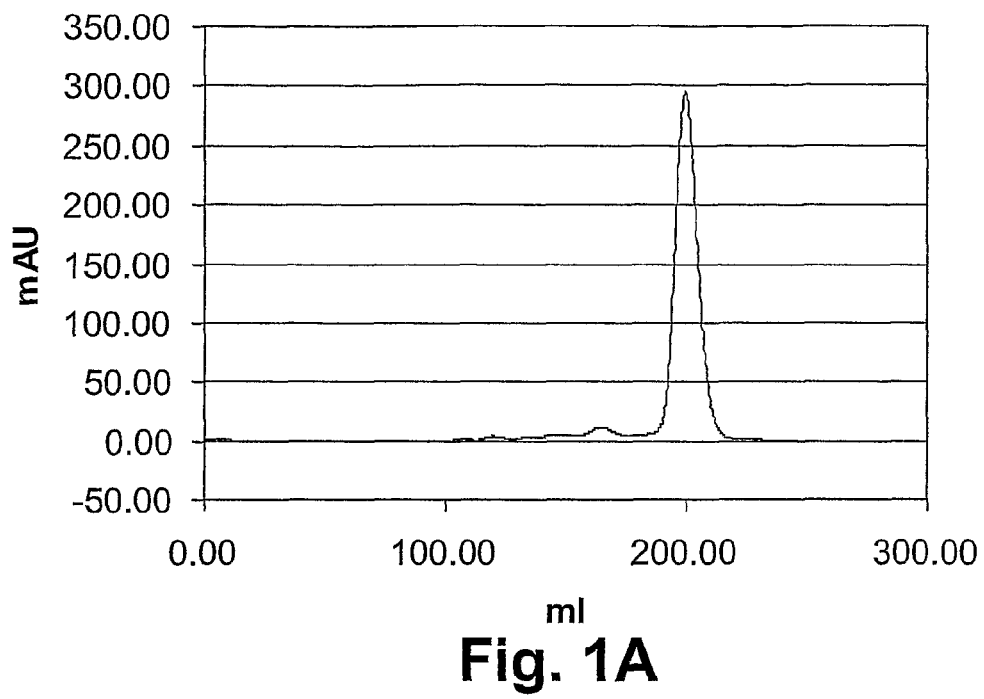
FIG. 1 shows the elution profiles of ESBA105 (FIG. 1A), TB-WT (FIG. 1B) and lucentis-scFv (FIG. 1C) of a preparative size exclusion chromatography (gel filtration) following the refolding step. mAU: milli-absorbance units.

The drops were applied on the top of the pupil and the eyelids were subsequently squeezed to remove excess fluid (7 mcl remaining). ESBA105 concentrations were determined in aqueous, vitreous and serum by ELISA.

FIG. 19 shows a graphical depiction of topical rabbit eye application in vivo results. One drop of 10 mg/ml ESBA105 solution was applied to the lower eye sac of both eyes of each animal five times a day for up to 6 days.

Sampling: After applying the second drop at the indicated time point (after 1, 3 or 6 days) two animals were sacrificed and both eyes, as well as the serum were subjected to quantitative ELISA analysis. ESBA105 levels in were determined in the aqueous (FIG. 19A), in the vitreous (FIG. 19 B), in the neuroretina (FIG. 19 C), in the choroidea (FIG. 19 D) and in the serum (FIG. 19 E) as indicated.

"Carr" stands for carrier, which means buffer solution without ESBA105. Data bars represent the maximal, the minimal and the median ESBA105 concentrations measured in the indicated compartments and are given together with the respective standard deviations.

DETAILED DESCRIPTION OF THE INVENTION

In order to provide a clear understanding of the specification and claims, the following definitions are conveniently provided below.

DEFINITIONS

The term "antibody" refers to whole antibodies and any antigen-binding fragment (i.e., "antigen-binding portion," "antigen-binding polypeptide," or "immuno-binder") or single chain thereof. An "antibody" refers to a glycoprotein comprising at least two heavy (H) chains and two light (L) chains inter-connected by disulfide bonds, or an antigen-binding portion thereof. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "antigen-binding" refers to the ability to specifically bind to an antigen. It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a single domain or dAb fragment (Ward et al., (1989) Nature 341:544-546), which consists of a VH domain; and (vi) an isolated complementarity determining region (CDR) or (vii) a combination of two or more isolated CDRs which may optionally be joined by a synthetic linker. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; and Huston et al. (1988) Proc. Natl. Acad. Sci. USA 85:5879-5883). These antibody fragments are obtained using conventional techniques known to those with skill in the art, and the fragments are screened for utility in the same manner as are intact antibodies.

As used, "immunoglobulin" may refer to any recognized class or subclass of immunoglobulins such as IgG, IgA, IgM, IgD, or IgE. The immunoglobulin can be derived from any species, such as human, murine, or rabbit origin. Further, the immunoglobulin may be polyclonal, monoclonal, or fragments. Such immunoglobulin fragments may include, for example, the Fab', F(ab')2, Fv or Fab fragments, or other antigen recognizing immunoglobulin fragments. Such immunoglobulin fragments can be prepared, for example, by proteolytic enzyme digestion, for example, by pepsin or papain digestion, reductive alkylation, or recombinant techniques. The materials and methods for preparing such immunoglobulin fragments are well-known to those skilled in the art (Parham, (1983) J. Immunology, 131:2895; Lamoyi et al., (1983) J. Immunological Methods, 56:235; Parham, (1982) J. Immunological Methods, 53:133; and Matthew et al., (1982) J. Immunological Methods, 50:239).

In addition the immunoglobulin may be a single chain antibody ("SCA"). These may consist of single chain Fv fragments ("scFv") in which the variable light ("VL") and variable heavy ("VH") domains are linked by a peptide bridge or by disulfide bonds. Also, the immunoglobulin may consist of single VH domains (dabs) which possess antigen-binding activity. See, e.g., G. Winter and C. Milstein, Nature, 349, 295 (1991); R. Glockshuber et al., Biochemistry 29, 1362 (1990); and, E. S. Ward et al., Nature 341, 544 (1989).

As used herein, the term "polypeptide" refers to a polymer of two or more of the natural amino acids or non-natural amino acids. The polypeptides of the invention comprise at least one amino acid sequence derived from an immunoglobulin (Ig) molecule. In one embodiment a polypeptide of the invention comprises an amino acid sequence or one or more moieties not derived from an immunoglobulin molecule. Exemplary modifications are described in more detail below. For example, in one embodiment, a polypeptide of the invention may comprise a flexible linker sequence. In another embodiment, a polypeptide may be modified to add a functional moiety (e.g., PEG, a drug, or a label).

Preferred polypeptides of the invention comprise an amino acid sequence derived from a human immunoglobulin sequence. However, polypeptides may comprise one or more amino acids from another mammalian species. For example, a primate heavy chain portion, hinge portion, or binding site may be included in the subject polypeptides. Alternatively, one or more murine amino acids may be present in a polypeptide. Preferred polypeptides of the invention are not immunogenic.

It will also be understood by one of ordinary skill in the art that the polypeptides of the invention may be altered such that they vary in amino acid sequence from the naturally occurring or native polypeptide from which they were derived, while retaining the desirable activity of native polypeptide. For example, nucleotide or amino acid substitutions leading to conservative substitutions or changes at "non-essential" amino acid residues may be made. An isolated nucleic acid molecule encoding a non-natural variant of a polypeptide derived from an immunoglobulin (e.g., an immunoglobulin heavy chain portion or light chain portion) can be created by introducing one or more nucleotide substitutions, additions or deletions into the nucleotide sequence of the immunoglobulin such that one or more amino acid substitutions, additions or deletions are introduced into the encoded protein. Mutations may be introduced by standard techniques, such as site-directed mutagenesis and PCR-mediated mutagenesis.

The polypeptides of the invention may comprise conservative amino acid substitutions at one or more non-essential amino acid residues. A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a nonessential amino acid residue in polypeptide is preferably replaced with another amino acid residue from the same side chain family. In another embodiment, a string of amino acids can be replaced with a structurally similar string that differs in order and/or composition of side chain family members. Alternatively, in another embodiment, mutations may be introduced randomly along all or part of the immunoglobulin coding sequence, such as by saturation mutagenesis, and the resultant mutants can be incorporated into polypeptides of the invention and screened for their ability to bind to the desired target.

The terms "specific binding," "selective binding," "selectively binds," and "specifically binds," refer to antibody binding to an epitope on a predetermined antigen. Typically, the antibody binds with an affinity (KD) of approximately less than 10-6 M, such as approximately less than 10-7 M, 10-8 M or 10-9 M or even lower.

The term "KD" refers to the dissociation equilibrium constant of a particular antibody-antigen interaction. Typically, the antibodies of the invention bind to their target antigen with a dissociation equilibrium constant (KD) of less than approximately 10-6 M, such as less than approximately 10-7 M, 10-8 M or 10-9 M or even lower, for example, as determined using surface plasmon resonance (SPR) technology in a BIACORE instrument.

The term "transit kinetics" or "pharmacokinetics" as used herein refers to all factors related to the dynamics of drug absorption, distribution in body tissues or fluids and metabolism and/or elimination. This involves the physicochemical factors that regulate the transfer of the polypeptide across membranes because the absorption, distribution, biotransformation and excretion of a polypeptide all involve the passage of the polypeptide across cell membranes.

Of great interest to the clinician is the bioavailability of a polypeptide. This term, as used herein, indicates the extent to which a polypeptide reaches its site of action or a biological fluid from which the polypeptide has access to its site of action. The factors affecting bioavailability include rate of absorption and metabolism or elimination of the polypeptide from the subject. Many factors affect absorption, these include the numerous physicochemical factors that affect transport across membranes such as a polypeptide solubility and uptake mechanisms as well as factors such as site of administration and the formulation (concentration) and composition of the polypeptide. The various routes of polypeptide administration have markedly different absorption characteristics. These routes include oral ingestion, pulmonary absorption, parenteral injection, including; intramuscular, subcutaneous, intravenous, intraarterial, intrathecal or intraperitoneal injection and topical application to mucous membranes, skin or eye. In a preferred embodiment, a polypeptide of the invention for treating eye disease is administered topically to the surface of the eye, e.g., in the form of eye drops. The transit kinetics of a polypeptide of the invention can be determined using, for example, any of the cell or animal based molecules disclosed herein, and are typically selected to be suitable for clinically relevant transit across the tight junctions of the blood brain barrier, intestine, or the eye.

The term "subject" is known in the art, and, as used herein, refers to a warm-blooded animal, more preferably a mammal, including, e.g., non-human animals such as rats, mice, rabbits, cats, dogs, sheep, horses, cattle, in addition to humans. In a preferred embodiment, the subject is a human. The subjects are those susceptible to treatment with a soluble antigen-binding polypeptide of the present invention.

A "penetration enhancing agent" or "penetration enhancer" as used herein, refers to molecules or compounds that promote transit across an epithelial junction. Penetration enhancing agents for use with the present invention include, but are not limited to, azone, benzalkonium chloride (BzCl), BL-7, BL-9, Brij 35, Brij 78, Brij 98, Brij 99, Polyoxyethylene-Polyoxypropylene 1800, sodium caprate, caprylic acid, cetylpyridinium chloride, chlorhexidine, cholate, castor oil, corn oil, cremophor-EL, DMSO, decamethonium bromide, deoxycholate, dextransulfate, EDTA, disodium EDETATE, ethanol, fusidate, glycocholate, lauryl sulfate, L-α-lysophosphatidylocholine, N-lauroylsarcosine, NMP, oleic acid, phospholipids, poly oxyethylene-9-lauryl ether, saponin, Tween 20, Tween 40, Tween 60, Tween 80, taurocholeate, and taurodeoxycholate. For example, in some embodiments, the penetration enhancing agent is sodium caprate. In other embodiments, the penetration enhancing agent is chlorhexidine.

In a first aspect of the present invention an scFv antibody is provided that specifically binds a selected antigen and has improved tissue penetration ability. Said antibody is characterized in that it is obtainable by a method comprising (i) selecting from a pool of soluble and stable frameworks the framework matching best to the framework with a non-human antibody of a selected antigen-binding specificity, (ii) either providing said framework with CDRs that bind said antigen or mutating the framework of said non-human antibody towards the sequence of said soluble and stable framework, (iii) testing the generated antibody for solubility and stability, and (iv) testing the generated antibody for antigen binding.

The term "matching best" means being as close as possible with respect to primary or tertiary structure.

In general, the antibody of the present invention comprises a framework with a VL and/or a VH domain, said framework being selected from at least part of a natural human antibody repertoire by an antigen independent method for high intracellular stability and solubility in a yeast cell. Said method is also known as the "quality control" screening of antibody frameworks and has resulted in a selection of particularly stable and soluble antibody frameworks that are characterized by high intracellular stability and solubility. These frameworks can be used for example in a second, yeast based screening system for antigen specificity. In this case, CDRs of a particularly stable and soluble antibody can be randomized and the resulting antibodies can be screened for best possible antigen recognition. Alternatively, known antibody CDRs of antibodies with strong binding affinity to an antigen of choice can be grafted onto said particularly stable and soluble frameworks. Optionally, said antibody can be further improved by mutagenesis of selected CDR(s) and/or framework, selecting improved clones in the "quality control system" (WO0148017, Auf der Maur et al. 2004), i.e. by mutating said scFv antibody by site-directed or random mutagenesis of one or more selected CDRs and/or the framework and selecting for stable and soluble antibodies under the same or under more stringent conditions. Selection can be done in vivo in the yeast quality control system.

The term "framework residues" relates to amino acid residues of antigen-binding polypeptide units, or the corresponding amino acid residues of antigen-binding polypeptide modules, which contribute to the folding topology, i.e. which contribute to the fold of said unit (or module) or which contribute to the interaction with a neighboring unit (or module). Such contribution might be the interaction with other residues in the unit (or module), or the influence on the polypeptide backbone conformation as found in α-helices or β-sheets, or amino acid stretches forming linear polypeptides or loops. The term "target interaction residues" refers to amino acid residues of the units, or the corresponding amino acid residues of the modules, which contribute to the interaction with target substances. Such contribution might be the direct interaction with the target substances, or the influence on other directly interacting residues, e.g. by stabilizing the conformation of the (poly)peptide of said unit (or module) to allow or enhance the interaction of said directly interacting residues with said target. Such framework and target interaction residues may be identified by analysis of the structural data obtained by the physicochemical methods referred to above, or by comparison with known and related structural information well known to practitioners in structural biology and/or bioinformatics. Such frameworks can also be referred to as scaffolds as they provide support for the presentation of the more divergent target interaction residues or CDRs.

CDRs or target interaction residues can be grafted into suitable frameworks, such as alternative scaffolds which are well-known in the art and include, but are not limited to, CTLA-4, tendamistat, fibronectin (FN3), neocarzinostatin, CBM4-2, lipocalins, T-cell receptor, Protein A domain (protein Z), Im9, designed ankyrin-repeat proteins (DARPins), designed TPR proteins, zinc finger, pVIII, avian pancreatic polypeptide, GCN4, WW domain, Src homology domain 3 (SH3), Src homology domain 2 (SH2), PDZ domains, TEM-1 β-lactamase, GFP, thioredoxin, staphylococcal nuclease, PHD-finger, CI-2, BPT1 APPI, HPSTI, ecotin, LACI-D1, LDTI, MTI-II, scorpion toxins, insect defensin A peptide, EETI-II, Min-23, CBD, PBP, cytochrome $b_{562}$, Ldl receptor domain A, γ-crystallin, ubiquitin, transferring, and C-type lectin-like domain (see Binz et al. (2005 October) *Nat Biotech* 23(10):1257-68), or into suitable frameworks of immunoglobulin-derived antigen-binding polypeptides which are well-known in the art and include, but are not limited to VhH domains, V-NAR domains, Vh domains, Fab, scFv, Bis-scFv, Camel IG, IfNAR, IgG, Fab2, Fab3, minibody, diabodies, triabodies and tetrabodies (see Holliger, P. and Hudson, P. (2005), Nat. Biotechnol. 23(9), pp. 1126-1136).

Preferably, the antibody of the present invention has one or more of the following further features:

it is stable under reducing conditions as measured in a yeast interaction assay, wherein the activity of a selectable marker protein fused to said scFv correlates with a high stability and solubility of said scFv in an intracellular environment. Said yeast interaction assay, the so-called "Quality control", was described in detail (Auf der Maur et al. (2001); Auf der Maur et al., 2004; the references being incorporated in their entirety herein).

is stable for at least 1 month, preferably at least two months, most preferred at least six months at 20° C. to 40° C., preferably at 37° C. in PBS, it remains monomeric under physiological conditions, it is soluble at ambient temperature in PBS at concentrations of >about 1 mg/ml, preferably of >about 4 mg/ml, more preferably of >about 10 mg/ml, even more preferably of >about 25 mg/ml and most preferably of >about 50 mg/ml, it reveals a midpoint of transition in a guanidinium hydrochloride titration of at least 1.5 M, preferably of at least 1.75 M, more preferably of at least 1.9 M, most preferably of at least 2 M, i.e. is resistant to denaturation.

The term antibody as used in the scope of the present invention refers to an scFv antibody or an antibody fragment that binds a selected antigen. Thus, the scFv antibody of the present invention can be either a full scFv comprising a VL and a VH domain which are linked by a short linker peptide, for example a linker comprising 1 to 4 repeats of the sequence GGGGS (SEQ ID NO: 22), preferably a (GGGGS)$_4$ peptide (SEQ ID No. 16), more preferably a linker of the sequence GGGGSGGGGSGGGGSSGGGS (SEQ ID No:17), or a linker as disclosed in Alfthan et al. (1995) Protein Eng. 8:725-731, or simply a VL or a VH domain, which has sufficient binding capacity for the selected antigen. The linkage of VL and VH can be in either orientation, VL-linker-VH or VH-linker-VL.

In one aspect the present invention provides an antibody which is stable for at least 1 month, preferably at least two months, in phosphate buffered saline (PBS). Preferably said antibody is tested for stability at physiological temperature, i.e. at 37° C. In another preferred embodiment said antibody is stable for at least 6 month when kept at 4° C. in PBS, or after lyophilization at room temperature. The stability can be tested for example by analyzing standard amounts of said antibodies by SDS polyacrylamide gel electrophoresis (PAGE) followed by a standard staining procedure, such a Coomassie staining or silver staining, and comparing the staining intensity of the full-length band with that of a standard protein. In addition, the absence of degradation products is checked. Degraded protein runs as a smear, or is even invisible due to the shortness of the degradation products, in which case only the loss of intensity of the full-length protein band indicates degradation. In general, a physical stability of an antibody can be assumed if no signs of aggregation, precipitation and/or denaturation upon visual inspection of color and/or clarity or as measured by UV light scattering or by size exclusion chromatography are observed.

The stability in terms of activity after a certain time of storage is a further important feature of the antibody of the present invention. It can be determined comparing the potency of the antibody before and after storage, for example in by in vitro target binding assays using ELISA or in vivo in cellular activity assays where the inhibition potency of the antibody is measured.

In another aspect the present invention provides an antibody which is and remains monomeric under physiological conditions, as can be judged e.g. by gel filtration. The monomeric state is an important feature of antibodies that are able to penetrate through epithelial barriers.

In a further aspect the present invention provides an antibody, which is soluble at ambient temperature in PBS at concentrations of greater than about 1 mg/ml, preferably of greater than about 4 mg/ml, most preferably of about 10 mg/ml. The solubility of the purified antibody can be determined by PEG precipitation using PEG3000, or by self-inter-action-chromatography (SIC)

In yet another aspect the present invention provides an antibody, which reveals a midpoint of transition in a guanidinium hydrochloride titration of at least about 1.5 M, preferably of at least about 1.75 M, more preferably of at least about 1.9 M, most preferably of at least about 2 M. This is a measure for stability in the sense of resistance towards unfolding, whereby the unfolding/denaturation induced by the addition of guanidinium hydrochloride is followed by fluoresces or circular dichroism spectroscopy.

In a further aspect of the present invention, the antibody having one or more of the afore mentioned biophysical characteristics is structurally characterized by a framework of the light chain variable domain (VL) of at least 85% similarity, preferably at least about 95% similarity, most preferably at least about 98% identity to a VL framework selected from the group comprising SEQ. ID. NO. 1 (kappa1 type), SEQ. ID. NO. 2 (kappa1 type), SEQ. ID. NO. 3 (kappa3 type) or SEQ. ID. NO. 4 (lambda1 type), SEQ ID No. 5 (kappa3 type), SEQ ID No. 6 (lambda3 type), or SEQ ID No. 7 (lambda3 type) and/or a framework of the heavy chain variable domain (VH) of at least 85% similarity, preferably at least about 95% similarity, most preferred at least about 98% identity to a VH framework selected from the group comprising Seq. Id. No. 8 (H3 type, SEQ ID No:9 (H3 type), SEQ ID No. 10 (H1b type), or SEQ ID No. 11 (H3 type). In a preferred embodiment, the combination between VL homologues of SEQ ID No:2 and VH homologues of SEQ ID No:8, combination between VL homologues of SEQ ID No:4 and VH homologues of SEQ ID No: 10, or combinations between homologues of anyone of the above mentioned VL sequences a VH homologue of SEQ ID No:9 are used. More preferred are antibodies with >90% similarity, and even more preferred with >95% similarity to SEQ ID No. 7. Most preferred are antibodies of the sequence SEQ ID No:7 and/or SEQ ID No:8. It is also understood that the invention encompasses any one of the VL sequences disclosed in combination with any one of the VH sequences disclosed so long as target binding specificity is maintained.

The percent similarity between two sequences is a measure of the extent to which protein sequences are related. The extent of similarity between two sequences can be based on percent sequence identity and/or conservation. Conservation refers to changes at a specific position of an amino acid sequence that preserve the physico-chemical properties of the original residue. The similarity between sequences is typically determined by sequence alignment.

The similarities referred to herein are to be determined by using the BLAST programs (Basic Local Alignment Search Tools; see Altschul, S. F., Gish, W., Miller, W., Myers, E. W. & Lipman, D. J. (1990) "Basic local alignment search tool." J. Mol. Biol. 215:403-410) accessible in Internet. BLAST protein searches can be performed with the XBLAST program, score=50, wordlength=3 to obtain similar amino acid sequences to the protein molecules of the invention. To obtain gapped alignments for comparison purposes, Gapped BLAST can be utilized as described in Altschul et al., (1997) Nucleic Acids Res. 25(17):3389-3402. When utilizing BLAST and Gapped BLAST programs, the default parameters of the respective programs (e.g., XBLAST and NBLAST) can be used. The percent identity between two sequences is a function of the number of identical positions shared by the sequences, taking into account the number of gaps, and the length of each gap, which need to be introduced for optimal alignment of the two sequences. The comparison of sequences and determination of percent identity between two sequences can be accomplished using a mathematical algorithm, which is well known to those skilled in the art.

The percent identity between two nucleotide sequences can be determined using the GAP program in the GCG software package, using a NWSgapdna.CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (CABIOS, 4:11-17 (1989)) which has been incorporated into the ALIGN program (version 2.0), using a PAM120 weight resi-due table, a gap length penalty of 12 and a gap penalty of 4. In addition, the percent identity between two amino acid sequences can be determined using the Needle-man and Wunsch (J. Mol. Biol. (48): 444-453 (1970)) algo-rithm which has been incorporated into the GAP program in the GCG software package, using either a Blossum 62 ma-trix or a PAM250 matrix, and a gap weight of 16, 14, 12, 10, 8, 6, or 4 and a length weight of 1, 2, 3, 4, 5, or 6.

In another aspect the antibody of the present invention is chemically modified. Chemical modifications may change properties of the antibody such as stability, solubility, antigen-binding specificity or affinity, in vivo half life cytotoxicity, and tissue penetration ability. Chemical modifications are well known to the skilled person. A preferred chemical modification of the antibody of the present invention is PEGylation.

In another preferred aspect, the affinity of the antibody of the present invention is characterized by a dissociation constant Kd of less than about 100 nM, preferably less than about 10 nM, and most preferably less than about 1 nM. Binding parameters such as affinity of the antibody to its cognate antigen are determined by surface plasmon resonance (BiaCore) or ELISA. These methods are well known in the art.

Preferably, the antigen that is bound by the antibody of the present invention is TNFα (tumour necrosis factor alpha). TNFα, also known as cachectin, is a naturally occurring mammalian cytokine produced by numerous cell types, including monocytes and macrophages in response to endotoxin or other stimuli. TNFα is a major mediator of inflammatory, immunological, and pathophysiological reactions (Grell, M., et al. (1995) Cell, 83: 793-802). A large number of disorders are associated with elevated levels of TNFα, many of them of significant medical importance. TNFα has been shown to be up-regulated in a number of human diseases, including chronic diseases such as rheumatoid arthritis (RA), inflammatory bowel disorders including Crohn's disease and ulcerative colitis, sepsis, congestive heart failure, asthma bronchiale and multiple sclerosis. TNFα is also referred to as a pro-inflammatory cytokine. However, it is also involved in disorders with a local manifestation, such as eye diseases, e.g. macular degeneration, uveitis, glaucoma, cataract, retinitis, dry eye syndrome, scleritis, conjunctivitis, and keratitis. The antibody of the present invention is particularly suitable for the treatment of such diseases, as it can be a applied locally and topically, for example for eye diseases by eye drops.

The present invention also provides a DNA sequence encoding the antibody of the present invention, as well as a cloning or expression vector containing said DNA sequence. In addition, a suitable host cell transformed with said DNA sequence is provided. This can be a prokaryotic or eukaryotic cell, in particular an *E. coli*, yeast, plant, insect or a mammalian cell.

The antibody of the present invention may be generated using routine techniques in the field of recombinant genetics. Knowing the sequences of the polypeptides, the cDNAs encoding them can be generated by gene synthesis.

Furthermore, a method for the production of the antibody of the present invention is provided, comprising culturing of the host cell transformed with the DNA encoding said antibody under conditions that allow the synthesis of said antibody, and recovering said molecule from said culture. Preferably, said method provides an scFv antibody purified from *E. coli* inclusion bodies or from the *E. coli* periplasm, if the scFv construct used comprises a signal sequence that directs the polypeptide to the periplasm.

Another aspect of the present invention is the use of the antibody provided by the present invention as a tool for diagnostics, preferably in vitro diagnostics, and/or as a pharmaceutical. This use is particularly preferred in the context of any TNFα related condition. The disease to be treated with an anti-TNFα scFv or fragment thereof is preferably a disease related to overexpression of TNFα. If overexpression of TNFα leads to an abnormal cellular function, an antibody that can bind and thus neutralize excess TNFα is an ideal pharmaceutical for the treatment of such disease, if said antibody can reach the place of TNFα excess. If this place is inside the cell, the antibody must be able to enter the cell. If this place is extracellular, the antibody must be able to reach the extracellular matrix in a tissue, i.e. it must cross at least the outermost cell layer of a tissue, which is usually the epithelial cell layer. In another embodiment of the present invention the antibody is able to penetrate the endothelium.

IV. Pharmaceutical Compositions and Pharmaceutical Administration

A. Compositions and Administration

In most cases the antibody of the present invention will be used in a pharmaceutical composition, said pharmaceutical composition comprising at least one further compound. Preferably, this will be in combination with a pharmaceutically acceptable carrier, diluent or excipient. The excipient may be selected from the group comprising azone, benzalkonium chloride (BzCl), BL-7, BL-9, Brij 35, Brij 78, Brij 98, Brij 99, Polyoxyethylene-Polyoxypropylene 1800, sodium caprate, caprylic acid, cetylpyridinium chloride, chlorhexidine, cholate, castor oil, corn oil, cremophor-EL, DMSO, decamethonium bromide, deoxycholate, dextransulfate, EDTA, disodium EDETATE, ethanol, fusidate, glycocholate, lauryl sulfate, L-α-lysophosphatidylocholine, N-lauroylsarcosine, NMP, oleic acid, phospholipids, poly oxyethylene-9-lauryl ether, saponin, Tween 20, Tween 40, Tween 60, Tween 80, taurocholeate, taurodeoxycholate, tight junction opening peptides and peptide derivatives, tight junction opening proteins and protein derivatives. Preferably, the excipient is selected from the group comprising benzalkonium chloride, Tween 20, Tween 40, Tween 60, Tween 80, and chlorhexidine. It is also possible to use caprate. Such substances can work as enhancers of penetration.

In most cases the pharmaceutical composition comprising the antibody of the present invention will be applied locally rather than systemically. The antibody of the present invention is particularly suitable for local application, as its scFv format is small, and its framework has physicochemical characteristics enabling it to penetrate epithelial tissue barriers. A local application is an application in a relatively restricted area such as it is the eye, the nasal cavity, the oral cavity, the intestinal tract, the skin, the mucosa of the mouth and the urogenital tract, e joints and joint spaces, the brain, the vertebra etc., where the application of a relatively small volume of sufficiently concentrated antibody is effective. On the other hand, topical application is an application to the surface of a body part.

The preferred form of administration of the pharmaceutical composition of the present invention is by topical application; however, other forms are by inhalation, e.g. if the antibody is destined to penetrate the lung epithelium. Pulmonary delivery may be accomplished using an inhaler or nebulizer and a formulation comprising an aerosolizing agent.

For topical applications, the preferred locus is the eye. The antibody of the present invention is particularly suitable to penetrate the cornea, which mainly consists of three tissue layers, namely the epithelium, the stroma and the endothelium. Thus the antibody can be used for the treatment of many diseases of the eye.

B. Drug Delivery Systems

Non-limiting examples of topical ocular drug delivery systems for use in the invention include penetration enhancers, corneal collagen shields, ocular iontophoresis, microparticles or nanoparticles, ocular inserts, mucoadhesive polymers, in situ gelling system, dendrimers, lipid emulsions, and ocular inserts (see Sultana, et al (2007) *Future Drugs,* 2(2), 309-323 (2007). i.

i. Penetration Enhancers

The pharmaceutical compositions of the invention may include a penetration enhancer. Examples of penetration enhancers are well-known in the art, and include Azone®, benzalkonium chloride (BzCl), BL-7, BL-9, Brij 35, Brij 78, Brij 98, Brij 99, Polyoxyethylene-Polyoxypropylene 1800, sodium caprate, caprylic acid, cetylpyridinium chloride, chlorhexidine, cholate, castor oil, corn oil, cremophor-EL, cyclodextrins, DMSO, decamethonium bromide, deoxycholate, dextransulfate, EDTA, disodium EDETATE, ethanol, fusidate, glycocholate, lauryl sulfate, L-α-lysophosphatidylocholine, methazolamide, N-lauroylsarcosine, NMP, oleic acid, Pz-peptide, phospholipids, poly oxyethylene-9-lauryl ether, saponin, Tween 20, Tween 40, Tween 60, Tween 80, taurocholeate, and taurodeoxycholate (see Sultana, et al. (2007) *Future Drugs*, 2(2), 309-323 (2007). In another embodiment, the penetration enhancer is sodium caprate. In yet another embodiment, the penetration enhancer includes colloidal systems, polyacrylates and bio-adhesive polymer. See also U.S. Ser. No. 60/958,942 (filed on Jul. 10, 2007). (entitled "Improved penetration Enhancers for the Delivery of Therapeutic Proteins" filed on Jul. 10, 2007).

ii. Corneal Collagen Shields

The antibodies of the invention can also be administered with a corneal collagen shield. In some embodiments, collagen shields with dissolution times of 12, 24 and 72 hours may be used. In other embodiments, the collagen shield is pre-soaked in solutions of gatifloxacin and/or moxifloxacin.

iii. Ocular Iontophoresis

The antibodies of the invention can also be delivered by ocular iontophoresis. In one embodiment, the antibodies may be delivered to the anterior segment of the eye by transcorneal iontophoresis. In another embodiment, the high and sustained concentrations of the antibodies of the invention may be delivered to the vitreous and retina by transscleral iontophoresis. Iontophoresis is applied for the desired duration of time. In some embodiments, iontophoresis is applied about 1 to about 4 minutes. In other embodiments, iontophoresis is applied less than 1 minute. In another embodiment, iontophoresis is applied for more than 4 minutes.

iv. Microparticles and Nanoparticles

The antibodies of the invention can also be delivered using microparticulate or nanoparticulate delivery systems. In some embodiments, the microparticle is a microcapsule. In other embodiments, the microparticle is a microsphere. In further embodiments, the microparticulate comprises polymers which are erodible, biodegradable, nonerodible, or ion exchange resins. In another embodiment, the microparticulate delivery system is Betoptic S®, containing betaxolol 0.25%.

Nanoparticles, particles smaller than 1 µm, can also be used. In one embodiment, the nanoparticle is a nanocapsule. In another embodiment, the nanoparticle is a nanosphere. In one embodiment, the nanoparticle comprises polyacrylcyanoacrylate (PACA). In another embodiment, the nanoparticle comprises poly-å-caprolactone. In certain embodiments, the nanoparticle comprises solid lipid nanoparticles containing 2.5% tobramycin with hexadecyl phosphate. In another embodiment, the nanoparticle comprises Eudragit RS 100 or Eudragit RL 100 and optionally further comprises cloricromene. In further embodiments, the nanoparticle includes flurbiprofen (FB)-loaded acrylate polymer nanosuspensions.

v. Ocular Inserts

The antibodies of the invention can also be administered using ocular inserts. In some embodiments, the ocular inserts are insoluble, soluble or bioerodible inserts. The insoluble inserts include diffusional systems, osmotic systems and hydrophilic contact lenses. The soluble inserts can be composed of natural, synthetic, or semisynthetic polymers. The bioerodible inserts can be composed of bioerodible polymers.

vi. Mucoadhesive Polymers

The pharmaceutical compositions of the invention may include mucoadhesive polymers. Examples of mucoadhesive polymers are well-known in the art, and include chitosan (CS), Ch-HCL and N-carboxymethylchitosan (CMCh), N-trimethyl chitosan (TMC) polymers, pilocarpine-loaded CS/Carbopol®, polyacrylic acid (PAA), polysaccharides, xyloglucan, tamarind seed polysaccharide (TSP), and thiolated polymers or thiomers.

vii. In Situ Gelling Systems

The pharmaceutical compositions of the invention may include in situ gelling systems. Examples of in situ gelling systems are well-known in the art, and include pH-mediated in situ gelling systems, temperature-mediated in situ gelling systems and ion-mediated in situ gelling systems. pH-mediated in situ gelling systems can include, for example, polymers such as cellulose acetate phthalate (CAP) and Carbopol®. Temperature-mediated in situ gelling systems can include, for example, pluronics, tetraonics and ethyl hydroxyethyl cellulose. In situ gelling systems may also include Gelrite® (deacetylated gellan gum (DCG)), alginates, e.g., alginate-poly(L-Lysine), timolol maleate ophthalmic solutions, e.g., Timoptol XE and Lizmon TG®, and combinations thereof.

viii. Dendrimers

The pharmaceutical compositions of the invention may include dendrimers. Examples of dendrimers are well-known in the art, and include TM polyamidoamine (PAMAM).

C. Formulations

In another embodiment, the formulation may be a slow, extended, or time release formulation, a carrier formulation such as microspheres, microcapsules, liposomes, etc., as known to one skilled in the art. Any of the above-mentioned delivery systems may be administered topically, intraocularly, subconjunctivally, or by implant to result in sustained release of the agent over a period of time. The formulation may be in the form of a vehicle, such as a micro- or macro-capsule or matrix of biocompatible polymers such as polycaprolactone, polyglycolic acid, polylactic acid, polyanhydrides, polylactide-co-glycolides, polyamino acids, polyethylene oxide, acrylic terminated polyethylene oxide, polyamides, polyethylenes, polyacrylonitriles, polyphosphazenes, poly(ortho esters), sucrose acetate isobutyrate (SAIB), and other polymers such as those disclosed in U.S. Pat. Nos. 6,667,371; 6,613,355; 6,596,296; 6,413,536; 5,968,543; 4,079,038; 4,093,709; 4,131,648; 4,138,344; 4,180,646; 4,304,767; 4,946,931, each of which is expressly incorporated by reference herein in its entirety, or lipids that may be formulated as microspheres or liposomes. A microscopic or macroscopic formulation may be administered topically or through a needle, or may be implanted. Delayed or extended release properties may be provided through various formulations of the vehicle (coated or uncoated microsphere, coated or uncoated capsule, lipid or polymer components, unilamellar or multilamellar structure, and combinations of the above, etc.). The formulation and loading of microspheres, microcapsules, liposomes, etc. and their ocular implantation are standard techniques known by one skilled in the art, for example, the use a ganciclovir sustained-release implant to treat cytomegalovirus retinitis, disclosed in Vitreoretinal Surgical Techniques, Peyman et al., Eds. (Martin Dunitz, London 2001, chapter 45); Handbook of Pharmaceutical Controlled Release Technology, Wise, Ed. (Marcel Dekker, New York 2000), the relevant sections of which are incorporated by reference herein in their entirety. For example, a sustained release intraocular implant may be inserted through the pars plana for implantation in the vitreous cavity. An intraocular injection may be into the vitreous (intravitreal), or under the conjunctiva (subconjunctival), or behind the eye (retrobulbar), or under the Capsule of Tenon (sub-Tenon), and may be in a depot form. The composition may be administered via a contact lens applied to the exterior surface of an eye, with the composition incorporated into the lens material (e.g., at manufacture, or contained in a lens solution). The composition may be administered via an intraocular lens (IOL) that is implanted in the eye. Implantable lenses include any IOL used to replace a patient's diseased lens following cataract surgery, including but not limited to those manufactured by Bausch and Lomb (Rochester N.Y.), Alcon (Fort Worth Tex.), Allergan (Irvine Calif.), and Advanced Medical Optics (Santa Ana Calif.). See also Degim, I. T and Celebi, N. (2007), Current Pharmaceutical Design, 13, 99-117]. When the lens is implanted within the lens capsule, the composition provides the desired effect to the eye. Concentrations suitable for implants (lenses and other types) and by contact lens administration may vary, as will be appreciated by one skilled in the art. For example, an implant may be loaded with a high amount of agent, but formulated or regulated so that a required concentration within the above-described ranges is sustainedly released (e.g., slow release formulation).

It has been found that antibody concentrations normally achieved with scFvs in the range of up to 1 mg/ml are not quite effective in epithelial penetration unless additional penetration enhancers are added (WO0040262). The present invention provides antibodies that are highly soluble, so that pharmaceutical compositions comprising said antibody at higher concentrations, i.e. greater than about 2 mg/ml, preferably greater than about 5 mg/ml, most preferably greater than about 10 mg/ml can be prepared and used in effective treatment of the corresponding, antigen related disease.

Hence, the present invention provides a method for the treatment of an antigen-related disease, wherein delivery of the antibody to the site of antigen-antibody interaction requires penetration of a tissue that comprises tight junctions, in particular an epithelium and/or an endothelium. An epithelium is a tissue composed of a layer of cells, and it lines both the outside (skin) and the inside (e.g. intestinum) of organisms. Epithelia also include the mucous membranes lining the inside of mouth and body cavities and comprise dead squamous epithelial cells, and epithelial cells lining the inside of the lungs, the gastrointestinal tract, and the reproductive and the urinary tracts. An endothelium is a layer of thin, flat cells that lines the interior surface of blood vessels and organs. In vasculature it forms an interface between circulating blood in the lumen and the rest of the vessel wall. Endothelial cells line the entire circulatory system, from the heart to the smallest capillary. In small blood vessels and capillaries, endothelial cells are often the only cell-type present. Endothelial cells also control the passage of materials into and out of the bloodstream. In some organs, there are highly differentiated endothelial cells to perform specialized 'filtering' functions. Examples of such unique endothelial structures include the renal glomerulus and the blood-brain barrier. Endothelial tissue is a specialized type of epithelium tissue.

In a preferred embodiment of the present invention, the penetration of the cornea can be achieved. The corneal epithelium covers the front of the cornea and consists of several layers of cells, which renders penetration by an antibody even more difficult. The antibody of the present invention is preferably able to penetrate the entire cornea.

An ideal drug for treatment of uveitis should cover four crucial characteristics: 1) Provide a fast onset of effects on acute symptoms. 2) Show comparable efficacy as compared with standard topical corticosteroids. 3) Show superior safety profile as compared with standard topical corticosteroids. 4) Have favourable pharmacokinetic properties allowing for topical application to the cornea as well as for intravitreal injection as compared with standard corticosteroids or standard monoclonal antibodies.

A locally applied inhibitor of TNFα, comprising adequate pharmacokinetic properties can address all these aspects. The good penetration of the anti-TNFα scFv antibody ESBA105 into the anterior part of the eye combined with its high TNFα-neutralizing activity ultimately lead to intra-ocular concentrations, which are very well suitable for therapeutic efficacy for uveitis anterior. Taken into account that TNFα levels found in the diseased eye were 15 pg/ml and that ESBA105 concentrations measured were up to 40,000 ng/ml for in the anterior part (see FIG. 7) and up to 125 ng/ml for vitreous part of the eye (see FIG. 8), we conclude that ESBA105 is not only suitable for the treatment of uveitis anterior, but also for the treatment of different forms of panuveitis like e.g. ocular Behçet's disease. The present invention thus provides an antibody for the treatment of ocular disorders by topical application to the eye, in particular for the treatment of any form of uveitis, Behçet's disease, retinitis, dry eye syndrome, glaucoma, Sjögren syndrome, diabetes mellitus (incl. diabetic neuropathy), scleritis, conjunctivitis and keratitis. Administration preferably occurs by eye drops, eye ointment, or from depot devices like contact lenses).

In another preferred embodiment of the present invention the antibody must penetrate the intestinal epithelium.

In the case of treatment in the lung, inhalation must be used to bring the antibody to apply the antibody of the present invention at the lung epithelium.

In yet another aspect of the present invention, the antibody is used as a diagnostic tool.

The sequences of the present invention are the following:

VL of the kappa1 type

SEQ. ID. No: 1

EIVMTQSPSTLSASVGDRVIITCRASQSISSWLAWYQQKPGKAPKLLIYK

ASSLESGVPSRFSGSGSGAEFTLTISSLQPDDFATYYCQQYKSYWTFGQG

TKLTVLG

VL of the kappa1 type

SEQ ID No: 2

EIVLTQSPSSLSASVGDRVTLTCRASQGIRNELAWYQQRPGKAPKRLIYA

GSILQSGVPSRFSGSGSGTEFTLTISSLQPEDVAVYYCQQYYSLPYMFGQ

GTKVDIKR

VL of the kappa3 type

SEQ ID No: 3

EIVMTQSPATLSVSPGESAALSCRASQGVSTNVAWYQQKPGQAPRLLIYG

ATTRASGVPARFSGSGSGTEFTLTINSLQSEDFAAYYCQQYKHWPPWTFG

QGTKVEIKR

VL of the kappa3 type

SEQ ID No: 4

EIVLTQSPATLSLSPGERATLSCRASQTLTHYLAWYQQKPGQAPRLLIYD

TSKRATGTPARFSGSGSGTDFTLTISSLEPEDSALYYCQQRNSWPHTFGG

GTKLEIKR

VL of the lambda1 type

SEQ ID No: 5

QSVLTQPPSVSAAPGQKVTISCSGSTSNIGDNYVSWYQQLPGTAPQLLIY

DNTKRPSGIPDRFSGSKSGTSATLGITGLQTGDEADYYCGTWDSSLSGVV

FGGGTKLTVLG

VL of the lambda3 type
SEQ ID No: 6
SYVLTQPPSVSVAPGQTATVTCGGNNIGSKSVHWYQQKPGQAPVLVVYDD
SDRPSGIPERFSGSNSGNTATLTIRRVEAGDEADYYCQVWDSSSDHNVFG
SGTKVEIKR VL of the lambda3 type
SEQ ID No: 7
LPVLTQPPSVSVAPGQTARISCGGNNIETISVHWYQQKLPGQAPVLVVSD
DSVRPSGIPERFSGSNSGNTATLTISRVEAGDEADYYCQVWDSSSDYVVF
GGGTKLTVLG VH of the H1b type
SEQ ID No: 8
QVQLVQSGAEVKKPGASVKVSCTASGYSFTGYFLHWVRQAPGQGLEWMGR
INPDSGDTIYAQKFQDRVTLTRDTSIGTVYMELTSLTSDDTAVYYCARVP
RGTYLDPWDYFDYWGQGTLVTVSS VH of the H3 type
SEQ ID No: 9
QVQLVQSGGGLVQPGGSLRLSCAASGFTFSSYAMSWVRQAPGKGLEWVSA
ISGSGGSTYYADSVKGRFTISRDNSKNTLYLQMNSLRAEDTAVYYCAAHV
LRFLEWLPDAFDIWGQGTLVTVSS VH of the H3 type
SEQ ID No: 10
EVQLVESGGGVAQPGGSLRVSCAASGFSFSSYAMQWVRQAPGKGLEWVAV
ISNDGRIEHYADAVRGRFTISRDNSQNTVFLQMNSLRSDDTALYYCAREI
GATGYLDNWGQGTLVTVSS VH of the H3 type
SEQ ID No: 11
EVQLVESGGGLVQPGGSLRLSCAASGFTFSSYAMSWVRQAPGKGLEWVSA
ISGSGGSTYYADSVKGRFTISRDNSKNTLYLQMNSLRAEDTAVYYCAKDA
GIAVAGTCFDYWGQGTLVTVSS TB-A
SEQ ID No: 12
DIVMTQSPSSLSASVGDRVTLTCTASQSVSNPVVWYQQRPGKAPKLLIYS
AFNRYTGVPSRFSGRGYGTDFTLTISSLQPEDVAVYYCQQDYNSPRTFGQ
GTKLEVKRGGGGSGGGGSGGGGSGGGGSQVQLVQSGAEVKKPGASVKVSC
TASGYTFTHYGMNWVRQAPGKGLEWMGWINTYTGEPTYADKFKDRFTFSL
ETSASTVYMELTSLTSDDTAVYYCARERGDAMDYWGQGTLVTVSS ESBA105
SEQ ID No: 13
DIVMTQSPSSLSASVGDRVTLTCTASQSVSNDVVWYQQRPGKAPKLLIYS
AFNRYTGVPSRFSGRGYGTDFTLTISSLQPEDVAVYYCQQDYNSPRTFGQ
GTKLEVKRGGGGSGGGGSGGGGSGGGGSQVQLVQSGAEVKKPGASVKVSC
TASGYTFTHYGMNWVRQAPGKGLEWMGWINTYTGEPTYADRFKDRFTFSL
ETSASTVYMELTSLTSDDTAVYYCARERGDAMDYWGQGTLVTVSS TB-WT
SEQ ID No: 14
DIVMTQTPKFLLVSAGDRVTITCTASQSVSNDVVWYQQKPGQSPKMLMYS
AFNRYTGVPDRFTGRGYGTDFTFTISSVQAEDLAVYFCQQDYNSPRTFGG
GTKLEIKRGGGGSGGGGSGGGGSGGGGSQIQLVQSGPELKKPGETVKISC KASGYTFTHYGMNWVKQAPGKGLKWMGWINTYTGEPTYADDFKEHFAFSL
ETSASTVFLQINNLKNEDTATYFCARERGDAMDYWGQGTSVTVSS scFv Lucentis
SEQ ID No: 15
DIQLTQSPSSLSASVGDRVTITCSASQDISNYLYQQKPGKAPKVLIYFTS
SLHSGVPSRFSGSGSGTDPTLTISSLQPEDFATYYCQQYSTVPWTFGQGT
KVEIKRGGGGSGGGGSGGGGSSGGGSEVQLVESGGGLVQPGGSLRLSCAA
SGYDFTHYGMNWVRQAPGKGLEWVGWINTYTGEPTYADDFKRRFTFSLDT
SKSTAYLQMNSLRAEDTAVYYCAKYPYYYTSSHWYFDVWGQGTLVTVSS linker
SEQ ID No: 16
GGGGSGGGGSGGGGSGGGGS linker
SEQ ID No: 17
GGGGSGGGGSGGGGSGGGGS ESBA105-QC15.2
SEQ ID No: 18
DIVMTQSPSSLSASVGDRVTLTCTASQSVSNDVVWYQQRPGKAPKLLIYS
AFNRYTGVPSRFSGRGYGTDFTLTISSLQPEDVAVYYCQQDYNSPRTFGQ
GTKLEVKRGGGGSGGGGSGGGGSSGGGSQVQLVQSGAEVKKGASVKVSCT
ASGYTFTHYGMNWVRQAPGRGLEWMGWINTYTGEPTYADKFKDRITFSLE
TSASTVYMELTSLTSDDTAVYYCARERGDAMDYWGQGTLVTVSS ESBA105-H_F68A
SEQ ID No: 19
DIVMTQSPSSLSASVGDRVTLTCTASQSVSVSNDVVWYQQRPGKAPKLLI
YSAFNRYTGVPSRFSGRGYGTDFTLTISSLQPEDVAVYYCQQDYNSPRTF
GQGTKLEVKRGGGGSGGGGSGGGGSSGGGSQVQLVQSGAEVKKPGASVKV
SCTASGYTFTHYGMWVRQAPGKGLEWMGWINTYTGEPTYADKFKDRATFS
LETSASTVYMELTSLTSDDTAVYYCARERGDAMDYWGQGTLVTVSS TB-H_F68V_F70L
SEQ ID No: 20
DIVMTQSPSSLSASVGDRVTLTCTASQSVSNDVVWYQQRPGKAPKLLIYS
AFNRYTGVPSRFSGRGYGTDFTLTISSLQPEDVAVYYCQQDYNSPRTFGQ
GTKLEVKRGGGGSGGGGSGGGGSSGGGSQVQLVQSGAEVKKPGASVKVSC
TASGYTFTHYGMNWVRQAPGKGLEWMGWINTYTGEPTYADKFKDRVTLSL
ETSASTVYMELTSLTSDDTAVYYCARERGDAMDYWGQGTLVTVSS TB-H_F70L
SEQ ID No: 21
DIVMTQSPSSLSASVGDRVTLTCTASQSVSNPVVWYQQRPGKAPKLLIYS
AFNRYTGVPSRLFSGRGYGTDFTLTISSLQPEDVAVYYCQQDYNSPRTFG
QGTKLEVKRGGGGSGGGGSGGGGSSGGGSQVQLVQSGAEVKKPGASVKVS
CTASGYTFTHYGMNWVRQAPGKGLEWMGWINTYTGEPTYADKFKDRFTLS
LETSASTVYMELTSLTSDDTAVYYCARERGDAMDYWGQGTLVTVSS

EXEMPLIFICATION

Throughout the examples, the following materials and methods were used unless otherwise stated.

Materials and Methods

In general, the practice of the present invention employs, unless otherwise indicated, conventional techniques of chemistry, molecular biology, recombinant DNA technology, immunology (especially, e.g., immunoglobulin technology), and animal husbandry. See, e.g., Sambrook, Fritsch and Maniatis, Molecular Cloning: Cold Spring Harbor Laboratory Press (1989); Antibody Engineering Protocols (Methods in Molecular Biology), 510, Paul, S., Humana Pr (1996); Antibody Engineering: A Practical Approach (Practical Approach Series, 169), McCafferty, Ed., Irl Pr (1996); Antibodies: A Laboratory Manual, Harlow et al, C.S.H.L. Press, Pub. (1999); Current Protocols in Molecular Biology, eds. Ausubel et al., John Wiley & Sons (1992)

Example 1

Production of scFvs

ScFv antibodies were produced via expression as inclusion bodies, followed by a refolding and a chromatography step. Three single-chain antibodies were produced. This includes two conventional scFvs, which presumably do not fulfill the criteria of being well soluble, particularly stable and monomeric. One of them is TB-wt (SEQ ID No: 14), which was constructed by linking the natural VL and VH sequences of the murine anti-TNFα monoclonal antibody Di62 (Doring et al., 1994). The other one is lucentis-scFv, which was constructed by linking the VL and VH sequences of the VEGF-specific Fab fragment ranibizumab (SEQ. ID. No:15). ESBA105 is an scFv, which carries the CDRs of Di62 and which reveals a Kd value in the nanomolar range for TNFα. Solubility, stability and monomeric behavior of ESBA105 were optimized by employing an scFv framework, which was selected by the so-called Quality Control system (Auf der Maur et al., 2004). The amino acid sequence of ESBA105 is disclosed in SEQ ID No. 13.

Figure 1B:
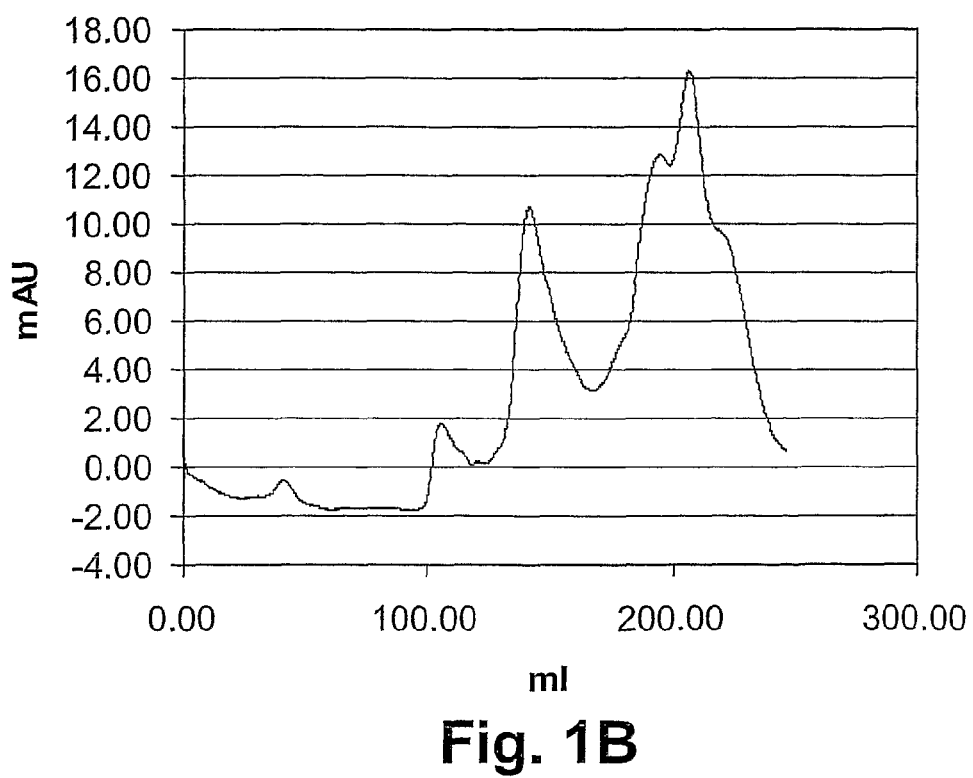
Figure 1C:
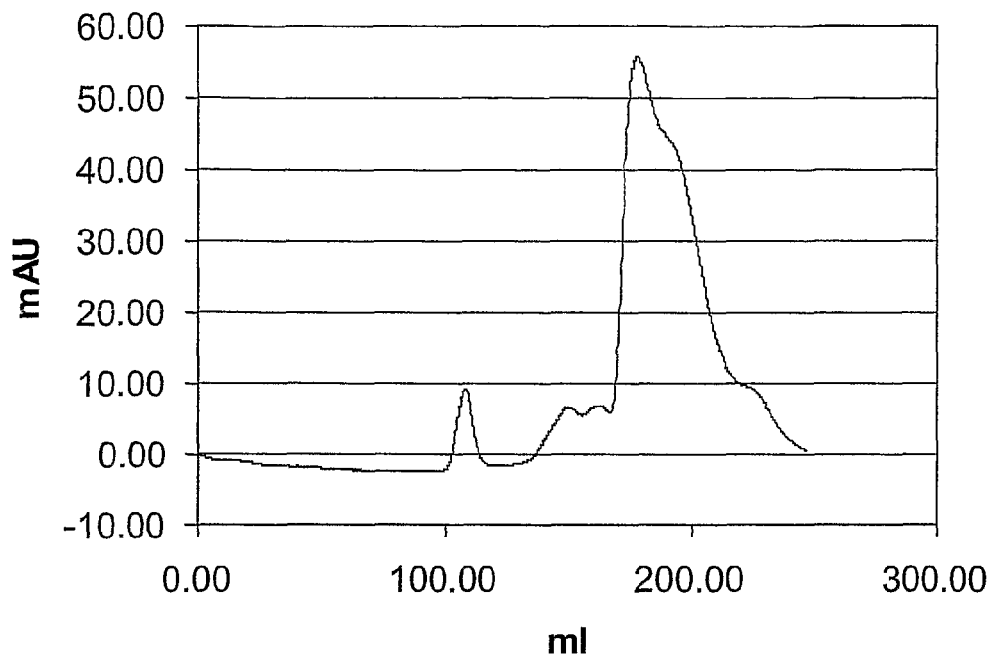
Figure 2:
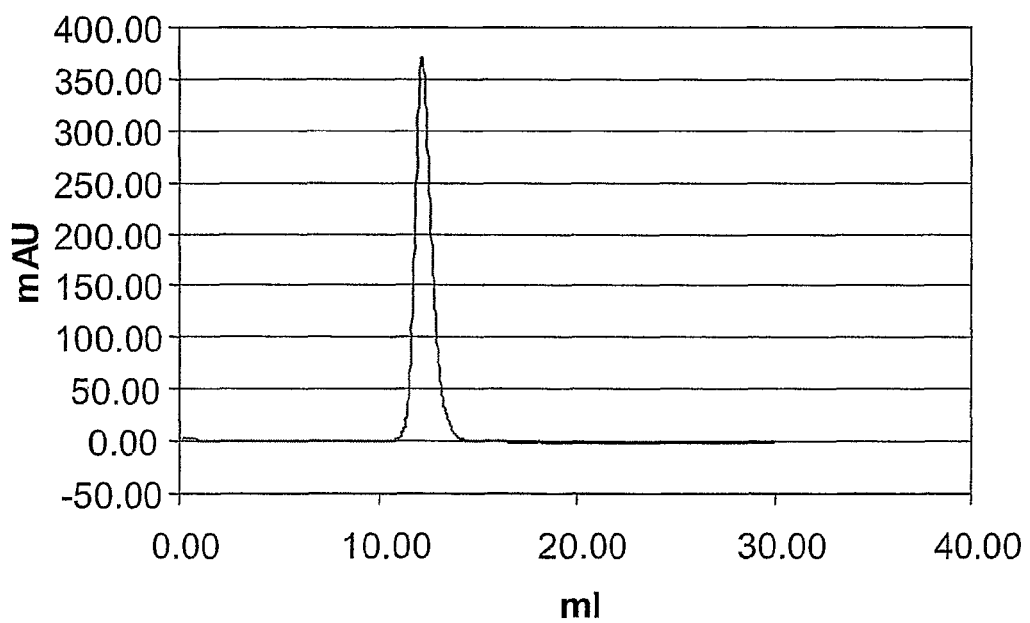
FIG. 2 shows the elution profile of an analytical gel filtration of the collected peak fractions of ESBA105 after preparative gel filtration.
Figure 3:
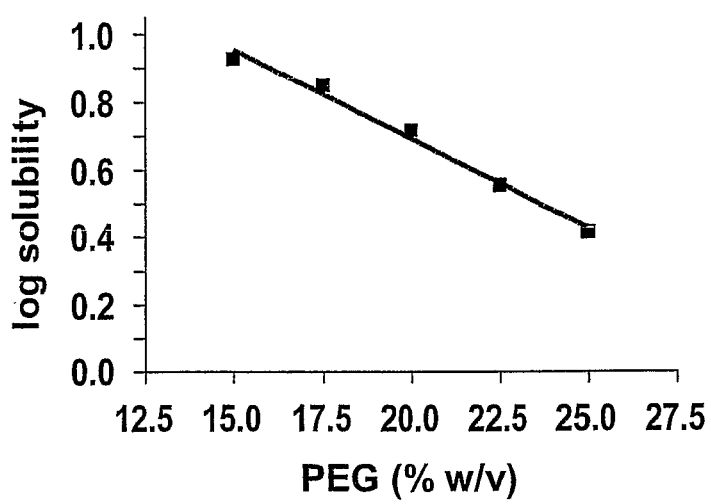
FIG. 3 shows the solubility of ESBA105 in polyethylene glycol (PEG).

FIG. 1 shows the elution profiles of ESBA105 (A), TB-wt (B) and lucentis-scFv (C) of the preparative gel filtration, which follows the refolding step. Whereas the profile for ESBA105 consists mainly of one sharp peak going up to 300 mAU (relative units for absorption), several broad peaks with maximal highs of 16 and 55 mAU, respectively, can be seen in the profiles of TB-wt and lucentis-scFv. This indicates that either the quality of the inclusion bodies and or the refolding process is much less efficient for TB-wt and lucentis-scFv as compared to ESBA105.

Below, the production procedure is described in detail for ESBA105.

Construction of Plasmid pGMP002 for Expression of ESBA105:

The ESBA105 coding sequence was ligated into the NcoI-HindIII sites of pET-24d(+) (Novagen, catalogue number 69752-3). Subsequently, the Bpu11021-NotI fragment of the resulting construct was removed by blunt end ligation after the sticky ends produced by Bpu11021 and NotI digestions were filled up by T4 polymerase reaction to produce pGMP003. pGMP002 was produced by removing the Bpu11021-NotI from pET-24d(+) directly.

Expression of ESBA105 in *E. coli*:

For expression of ESBA105, *E. coli* BL21 (DE3) (Novagen) was transformed with the expression plasmid pGMP002. Glycerol stock cultures were prepared from single colonies, cultivated in M9 medium (Sambrook et. al, Molecular Cloning, A laboratory Manual) containing 1% glucose, 1 ml/l of a trace element solution (Wang and Lee, Biotechnol Bioeng 58:325-328) and 50 µg/ml kanamycin. Cells were grown overnight at 37° C., glycerol was added to 20% and 1 ml aliquots were stored as glycerol stocks at −80° C.

For the first preculture, 50 ml of a synthetic defined medium (Korz et. al., J. Biotechnol. 1995, 39:59-65), containing 1% glucose, 1 ml/l of trace element solution and 50 µg/ml kanamycin, was inoculated with 1 ml of a glycerol stock. Preculture was grown overnight at 37° C. and 200 rpm in a baffled shake flask. A second preculture with 250 ml of the same medium was inoculated with the first preculture and grown for additional three hours at 37° C.

Bioreactor cultivations were performed in a 5 l bioreactor (BioFlo 110, New Brunswick Scientific), containing an initial volume of 3 l of the same synthetic medium used for precultures. Cultivation temperature was set to 37° C. Culture pH was controlled at 7.0 by the addition of 25% ammonia water and 1 M phosphoric acid. The level of dissolved oxygen was maintained above 20% of the air saturation level by varying the pure oxygen percentage at an overall aeration rate of 4 l/min. The bioreactor was inoculated with the second preculture and operated in batch mode up to an $OD_{600}$ of 10-12. Exponential glucose feeding was then started at a rate of 0.15 $h^{-1}$ with a 50% glucose solution containing 10 g/l $MgSO_4 \cdot 7H_2O$ and 5 ml/l trace element solution. After 16 h, protein expression was induced by addition of IPTG to 1 mM and exponential feeding was continued for 3 h. Cells were then harvested by centrifugation at 4,600 rpm for 1 h.

Inclusion Body Preparation:

For preparation of inclusion bodies, 1 kg of wet cell paste was resuspended in 5 l TBS buffer (10 mM Tris, 150 mM NaCl, pH 7.3). 1 g of solid lysozyme was added and cell suspension was incubated for 30-60 min. For cell disruption, the suspension was passed two times through a high-pressure homogenizer (Niro Soavi, Panda 2K) at 1,000 bar. Disrupted cells are centrifuged for 1 h at 4,600 rpm and the resulting inclusion bodies were resuspended in 2 l TBS buffer, containing 0.5% LDAO (N—,N-Dimethyldodecylamin-N-oxid, Fluka). The inclusion bodies were washed repeatedly until no significant residual protein was detected in the washing supernatant. Finally, inclusion bodies were washed twice with TBS-buffer without LDAO.

Refolding of ESBA105:

Inclusion bodies were solubilized in the 10-fold volume of solubilization buffer containing 6 M guanidinium-HCl, 100 mM Tris, 1 mM EDTA and 20 mM DTT at pH 8.0 and incubated overnight at room temperature. Solubilized protein was then refolded by 1:50 dilution into refolding buffer containing 3 M urea, 100 mM Tris and 2 mM each of cystein and cystine at pH 8.5. Refolding was continued for 24 h at room temperature. After refolding, precipitates were removed by depth filtration and the refolding solution was concentrated to 50% of the initial volume. The concentrated refolding solution was then dialyzed against the 4-fold volume of PBS buffer (50 mM Na-phosphate, 150 mM NaCl, pH 6.5) and further concentrated to a protein concentration of approximately 1 mg/ml.

Purification of ESBA105 by Chromatography:

ESBA105 was purified in two chromatography steps: gel filtration and cation exchange chromatography. All chromatography steps were operated by ÄKTA purification systems (GE Healthcare).

For preparative gel filtration chromatography, a Sephadex S75 26/60 column (GE Healthcare) was used with PBS buffer (50 mM Na-phosphate, 150 mM NaCl, pH 6.5) as running buffer. Collected ESBA105-fraction was eluted at approximately 185 ml retention volume as a single peak.

Fractogel EMD $SO_3^-$ (M) (Merck) was used as column resin for the second chromatography step. Resin was equilibrated with five column volumes equilibration buffer (50 mM Na-acetate, pH 5.5). ESBA105 peak fractions from gel filtration were diluted 10 fold with 50 mM Na-acetate pH 5.5 and then loaded onto the column with a flow rate of 5 ml/min. After loading, the column was washed with five column volumes equilibration buffer. A linear gradient from 0-35% Elution buffer (50 mM Na-acetate, 500 mM NaCl, pH 5.5) within 60 minutes and 5 ml/min was used for elution of ESBA105. The most prominent peak after elution was collected and identified as ESBA105. The collected ESBA105 fraction was finally dialyzed against PBS (50 mM Na-phosphate, 150 mM NaCl, pH 6.5) and stored at −80° C.

Example 2

Biophysical Characterization of scFvs

In order to investigate their "drug-likeness", ESBA105 and some of its derivatives were biophysically characterized. Characterization involved the determination of (1) solubility parameters (PEG precipitation and $B_{22}$ value; the B22 value is a measure for protein self-interaction, which is important in protein crystal growth, solubilisation and aggregation. See Valente et al., Biophys J. 2005 December; 89(6):4211-8. Epub 2005 Sep. 30), (2) the pI values, (3) the measurement of thermal and chaotropic denaturation, and (4) the quantification of the monomeric fraction as compared the oligomeric fraction. The results of items 1-3 are summarized in Table 1, which also includes relative potency values as determined by the L929 and the KYM-L1 assay, respectively.

TABLE 1

Summary of data on some ESBA105 derivatives.

| SEQ | pI | $S_{max}$ (PEG prec.) | $B_{22}$ value (SIC) |
|---|---|---|---|
| ESBA105 | 7.8 | 1.839 ± 0.133 | $-24.5 \times 10^{-4} \pm 3.8 \times 10^{-4}$ |
| ESBA105-QC2.2 | 7.8 | nd | nd |
| ESBA105-QC7.1 | | nd | nd |
| ESBA105-QC11.2 | 8.2 | 1.913 ± 0.091 | $1.59 \times 10^{-3} \pm 5.9 \times 10^{-5}$ |
| ESBA105-QC15.2 | 7.8 | 1.857 ± 0.02 | $1.28 \times 10^{-3} \pm 3.0 \times 10^{-4}$ |
| ESBA105-QC23.2 | 7.8 | 1.881 ± 0.068 | $1.06 \times 10^{-4} \pm 2.9 \times 10^{-5}$ |
| ESBA105-H_F68A | 7.8 | nd | nd |
| TB-H_F68V_F70L | 7.8 | nd | nd |
| TB-H_F70L | 7.8 | nd | nd |

| SEQ | Onset of denaturation [° C.] | [GdnHCl] at midpoint of unfolding | Relative potency: $EC_{50}X/EC_{50}ESBA105$ L929 cells | KYM-1 cells |
|---|---|---|---|---|
| ESBA105 | 53 | 2.07 M | 1.0 | 1.0 |
| ESBA105-QC2.2 | 58 | nd | 1.1 | 1.6 |
| ESBA105-QC7.1 | | nd | nd | nd |
| ESBA105-QC11.2 | 58 | 2.33 M | 0.8 | 1.3 |
| ESBA105-QC15.2 | 26 | 2.30 M | 1.37 | 1.5 |
| ESBA105-QC23.2 | 58 | nd | 1.32 | 1.5 |
| ESBA105-H_F68A | nd | nd | 1.14 | nd |
| TB-H_F68V_F70L | nd | nd | 1.28 | nd |
| TB-H_F70L | nd | nd | 2.7 | nd |

Example 3

Stability of scFv During Storage

Figure 4:
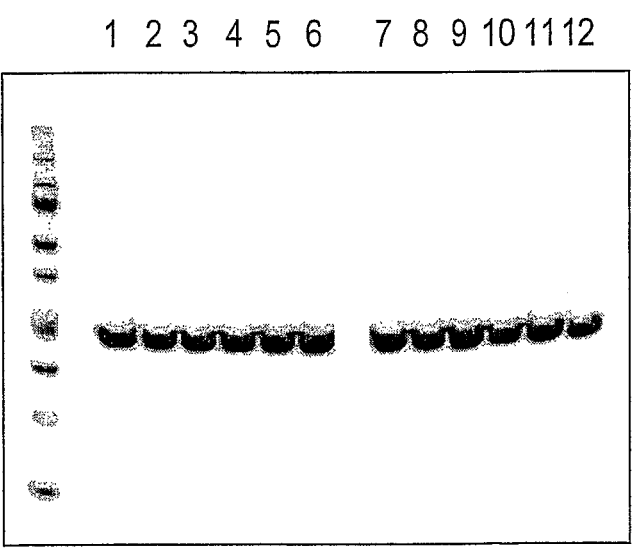
FIG. 4 shows the stability of ESBA105 and QC 15.2 scFv antibodies when stored for two weeks at different temperatures and concentrations. Antibodies were separated by SDS PAGE and stained with Coomassie brilliant blue.

The stability of the scFv over time is an important feature in the context of a pharmaceutical. FIG. 4 shows an analysis of the ESBA105 scFv (lanes 1-6) and the QC15.2 scFv (lanes 7-12) that were separated by SDS-PAGE and stained with Coomassie after two weeks of storage at different temperature (−80° C.: lanes 1, 3, 5, 7, 9, and 11) or 40° C.: lanes 2, 4, 6, 8, 10 and 12) and concentrations (20 mg/ml: lanes 1, 2, 7 and 8; 10 mg/ml; lanes 3, 4, 9 and 10; 1 mg/ml: lanes 5, 6, 11 and 12). The antibodies remained stable over the entire ranges of temperature and at all tested concentrations, and no signs of degradation or aggregation were found.

Figure 5:
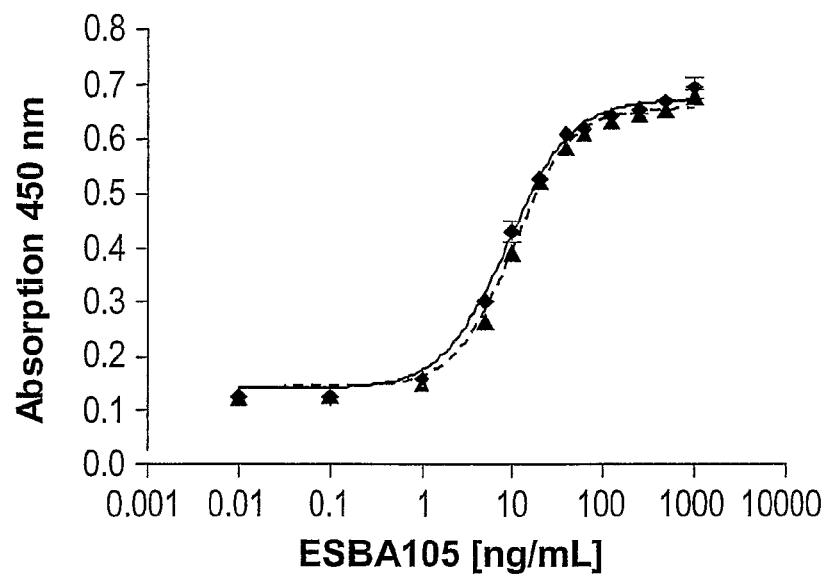
FIG. 5 shows the activity of ESBA105 determined by an L929 assay after 8 weeks of storage at either 37° C. or −80° C., both at pH 7.4. Triangles indicate ESBA105 stored at 37° C. and squares ESBA105 stored at −80° C.

An antibody that is stable over a certain time should also retain its full activity. Therefore, we tested ESBA105 eight weeks after storage at 37° C. or −80° C. in L929 assays for their activity. The result is presented in FIG. 5, and no difference between the two temperatures could be seen.

Example 4

Ex Vivo Penetration of ESBA105 into Whole Rabbit Eyes

Figure 6:
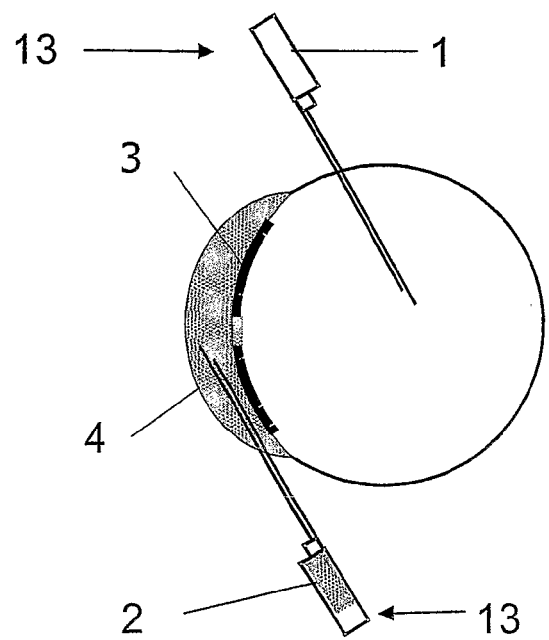
FIG. 6 shows schematically syringes removing liquid from vitreous and from anterior chamber, respectively. 1 vitreous cavity liquid, 2 anterior eye liquid, 3 iris, 4 cornea, 13 syringe.

The amount of ESBA105 penetrating into different compartments of whole rabbit eyes was tested under various conditions in an ex vivo setting. For these series of experiments, the rabbit eyes were placed on incubation test plates that have depressions on its surface. The depression contained the ESBA105 test solution and the rabbit eyes were placed on the test plates such that the cornea was in contact with the test solution. After an incubation time of 4 hours at 37° C., the different eye compartments were analyzed for their ESBA105 content. For this analysis, a syringe was used to remove probes from the compartment of interest (see FIG. 6) and the ESBA105 concentration of the probe was determined by ELISA.

Figure 7:
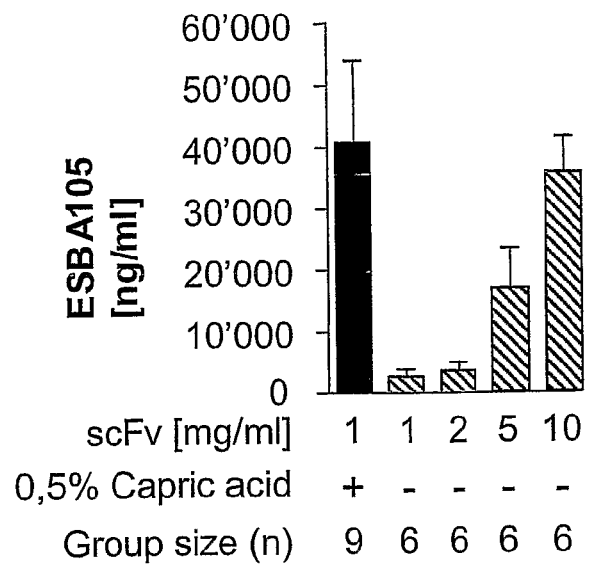
FIG. 7 shows penetration of ESBA105 into the anterior chamber of intact rabbit eyes after 4 hours.
Figure 8:
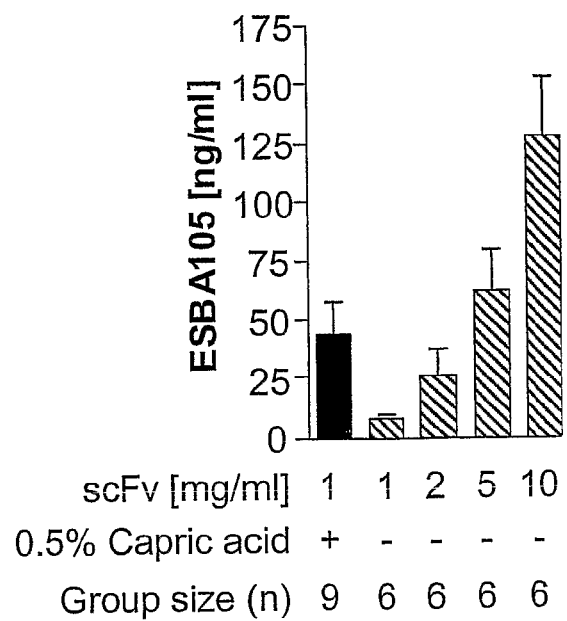
FIG. 8 shows penetration of ESBA105 the vitreous cavity of intact rabbit eyes after 4 hours.

The following conditions were assessed with the experimental setup described above: ESBA105 was tested at concentrations of 1, 2, 5 and 10 mg/ml. The concentration of 1 mg/ml was furthermore tested in the presence of 0.5% capric acid. 0.5% of capric acid was previously shown by Thiel et al. (Clin. Exp. Immunol. 2002 April; 128 (1):67-74) to enhance the penetration through cornea. When 1 mg/ml was administered in the presence of 0.5% capric acid, we measured a concentration of ESBA105 in the anterior part of the eye of about 40 μg/ml, which was about the same as compared to concentrations measured after administration of 10 mg/ml in the absence of capric acid (FIG. 7). Interestingly, when the results of these two administration modes were compared in the vitreous liquid, there were about 40 ng/ml measured for administration of 1 mg/ml with capric acid and about 125 ng/ml for 10 mg/ml without capric acid (FIG. 8). In the absence of capric acid the concentrations measured in the two compartments revealed a clear dependence on the applied concentrations of 1, 2, 5 and 10 mg/ml (FIG. 8).

The eye incubation test plates were pre-incubated with blocking buffer (5% low fat milk powder in PBS, pH 7.4) overnight at 4° C. On the next day the plates were washed with PBS and afterwards dried by incubating at 37° C. for 30 minutes. The wells of the dried plates were filled with 125 μl of test solution each and isolated rabbit eyes were placed to the wells in a manner that only the cornea was in contact with the test solution. After incubation at 37° C. and 100% humidity for 4 hours, the eyes were washed for 3 hours with PBS.

Paracenthesis was carried out using a 25 G needle for the anterior eye chamber and a 22 G needle for the vitreous body.

The concentration of ESBA105 in the probes was determined by ELISA as follows: The probes were centrifuged with a bench-microfuge at 13,000 rpm for 5 min at room temperature. The probes from the anterior compartment were diluted 1:10, 1:100 and 1:1000, the probes from the vitreous compartment were diluted 1:5 in TBST (TBS supplemented with 0.005% Tween) containing 0.5% low fat milk powder (hereinafter referred to as diluting solution) for ELISA testing.

ELISA 96 well plates (Nunc Maxisorb; catalogue number 442404) were coated with 0.5 μg/ml human TNFα over night at 4° C. On the next day the plates were washed 3 times with TBST at room temperature and incubated with 300 μl blocking buffer (5% low fat milk powder in TBST) per well for 60 min at room temperature on a shaker (500-600 rpm). After the blocking step the plates were washed 3 times with TBST before 50 μl of diluted probes were added to each well and the plates were incubated on a shaker (500-600 rpm) for 90 minutes at room temperature. After this incubation step the plates were washed 3 times with TBST, before 50 μl of a 1:10,000 solution (diluted in diluting solution) of the secondary antibody AKA3A-biotinylated were added to each well. AKA3A-biotinylated is a polyclonal rabbit anti-ESBA105 antibody, which was freshly biotinylated (according to standard biotinylation protocols). After 90 minutes of incubation on a shaker (500-600 rpm) at room temperature, the plates were washed 3 times with TBST, before 50 μl of a 1:2000 dilution (diluted in diluting solution) of streptavidin-coupled horseradish peroxidase (streptavidin-polyHRP40, 1 mg/ml; SDT; #SP40C) was added. After 60 minutes of incubation on a shaker (500-600 rpm) at room temperature, the plates were washed 3 times with TBST and 2 times with ddH$_2$O. Horseradish peroxidase (HRP) activity was detected upon addition of 50 μl BM Blue POD substrate (Roche Diagnostics, catalogue number 1484281) to each well. After 6-12 minutes of incubation at room temperature in the dark the HPR reaction was stopped by addition of 50 μl 1 M HCl to each well. The HPR reaction was quantified by spectrometric measurement at 450 nm in a TECAN Genios reader.

The ESBA105 concentration of the probes was finally determined by comparison to a standard curve, which was produced in parallel.

Example 5

Penetration Through Caco-2 Cell Monolayers by ESBA105

Figure 9:
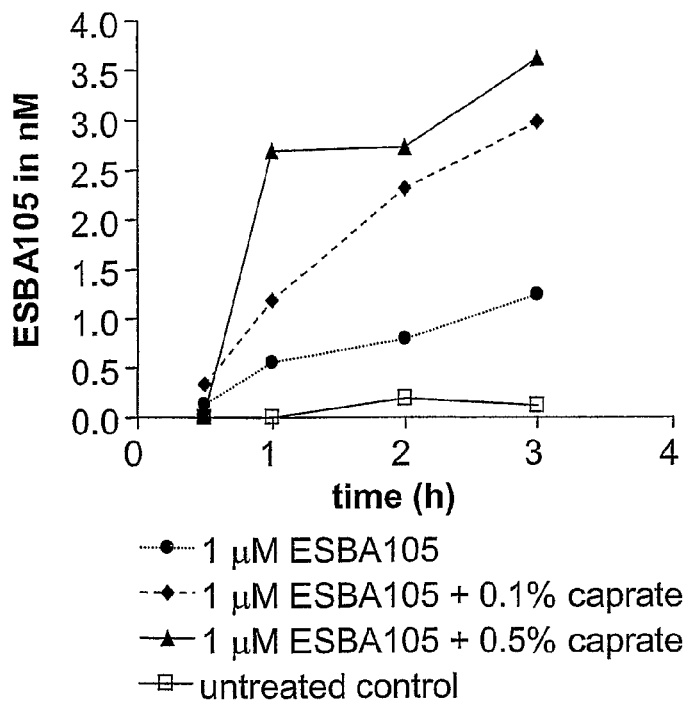
FIG. 9 shows penetration of ESBA105 across a Caco-2 cell layer.
Figure 10:
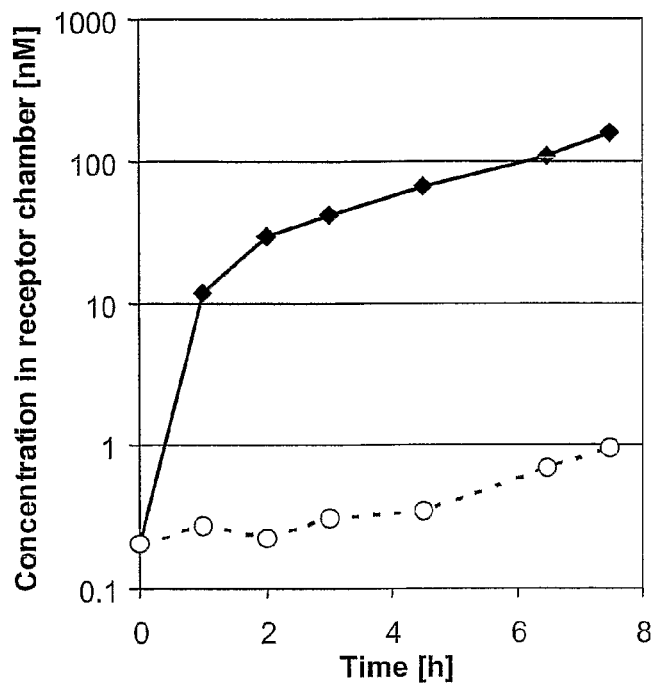
FIG. 10 shows a comparison of penetration efficacies of a full-length IgG format antibody (Infliximab) and a single-chain format antibody fragment (ESBA105) through rat jejunum in the non-everted sac model for intestinal drug absorption. Black squares indicate the ESBA105 concentration in nM, white circles the infliximab concentration in nM.
Figure 11D:
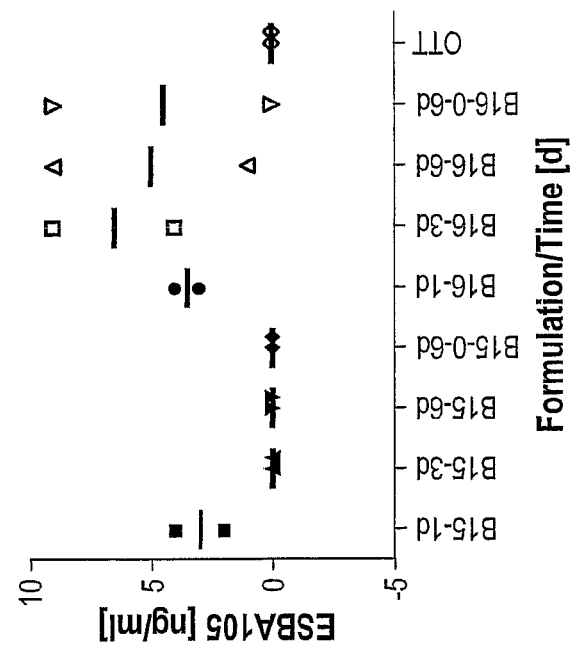
FIG. 11d is a graphical depiction of the amount of ESBA105 in ng/ml found in the serum of the rabbit eyes sampled over the course of the study described in Example 7.
Figure 11C:
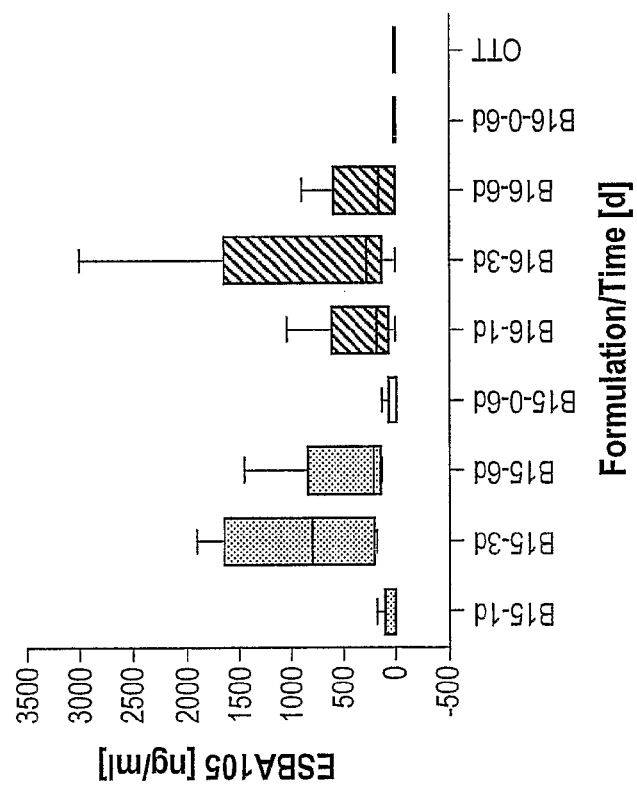
FIG. 11c is a graphical depiction of the amount of ESBA105 in ng/ml found in the neuroretina of the rabbit eyes sampled over the course of the study described in Example 7.
Figure 12:
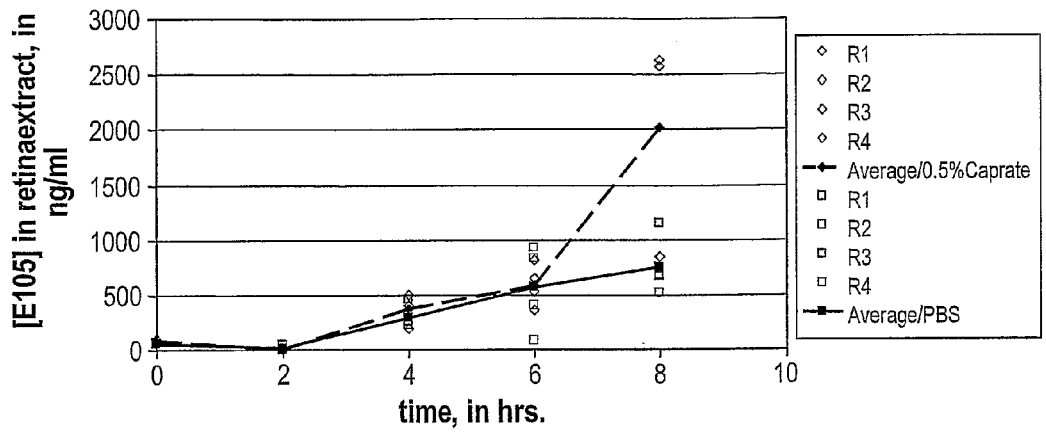
FIG. 12 is a graphical depiction of the local in vitro pK of ESBA105 in rabbit eyes. Retina extract ~500 ng/ml. 060721 ELISA (from #060718 Whole Eye Rabbit), Retina.
Figure 13:
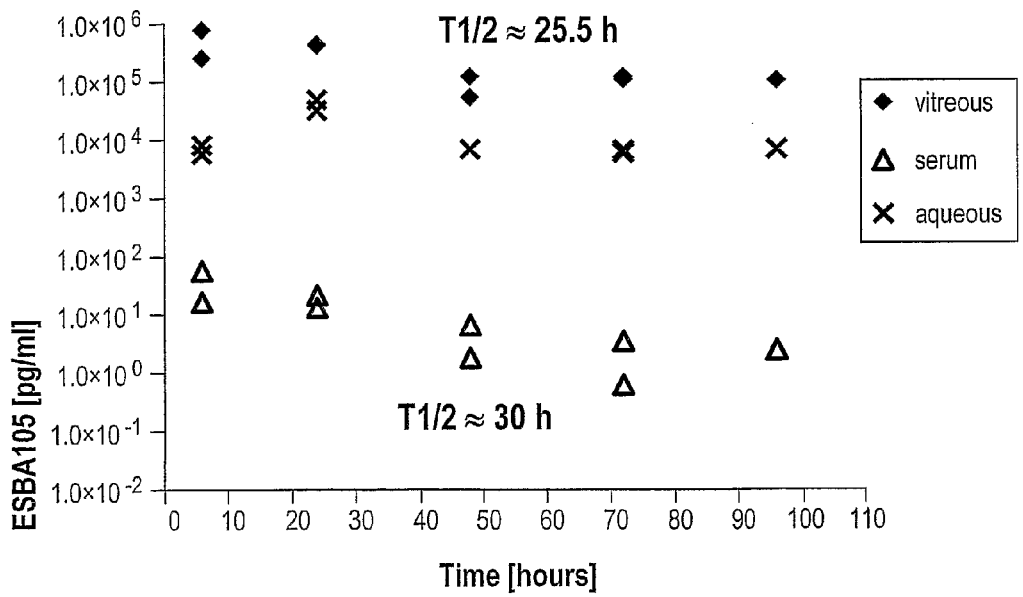
FIG. 13 is a graphical depiction of the local half-time of ESBA105 upon vitreal injection in rabbit eyes.
Figure 14:
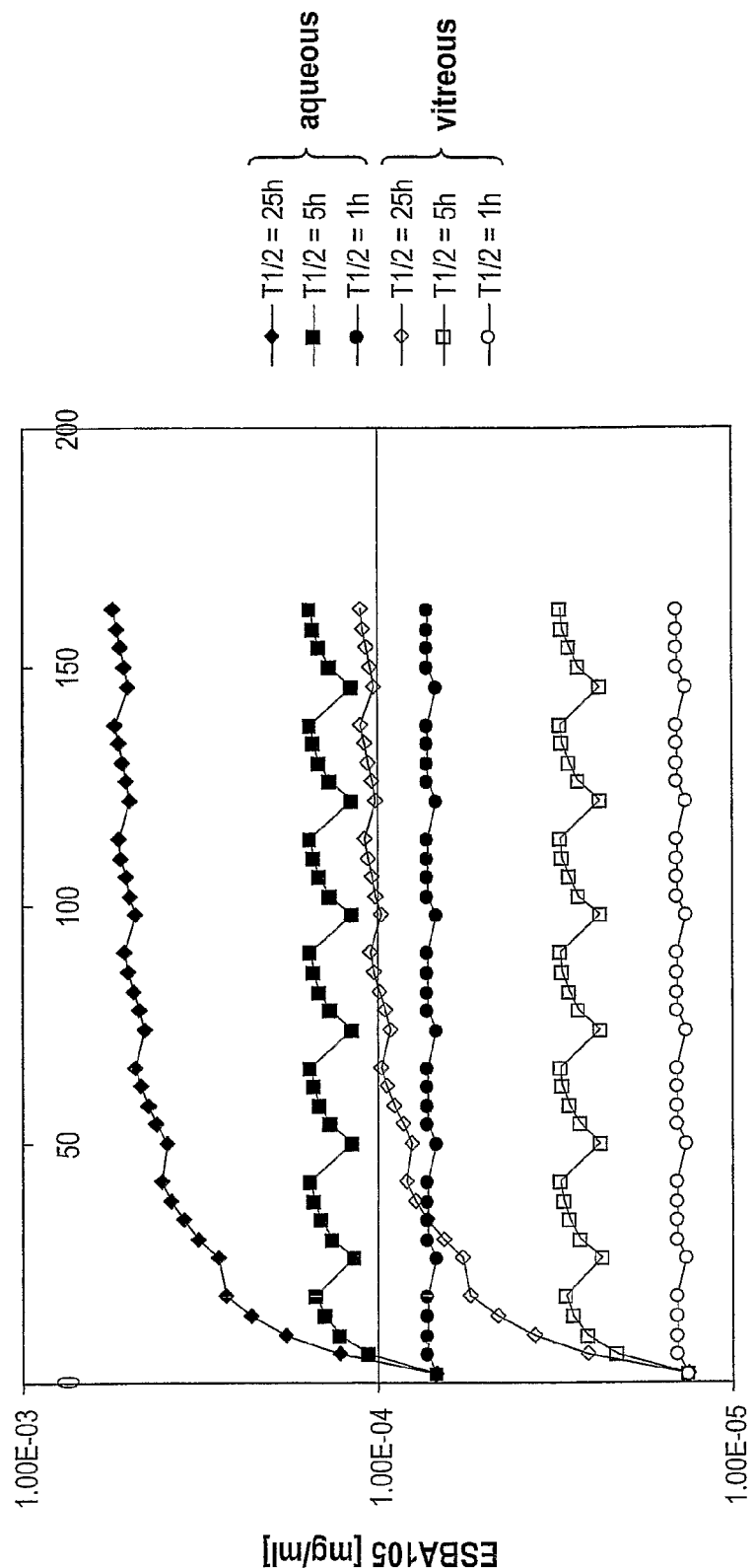
FIG. 14 is a graphically depicts the modeling of local drug accumulation after administration of ESBA105 (5 drops/day, 10 mg/ml ESBA105, $P_{eff}=2.9\times10^{-5}$).
Figure 15:
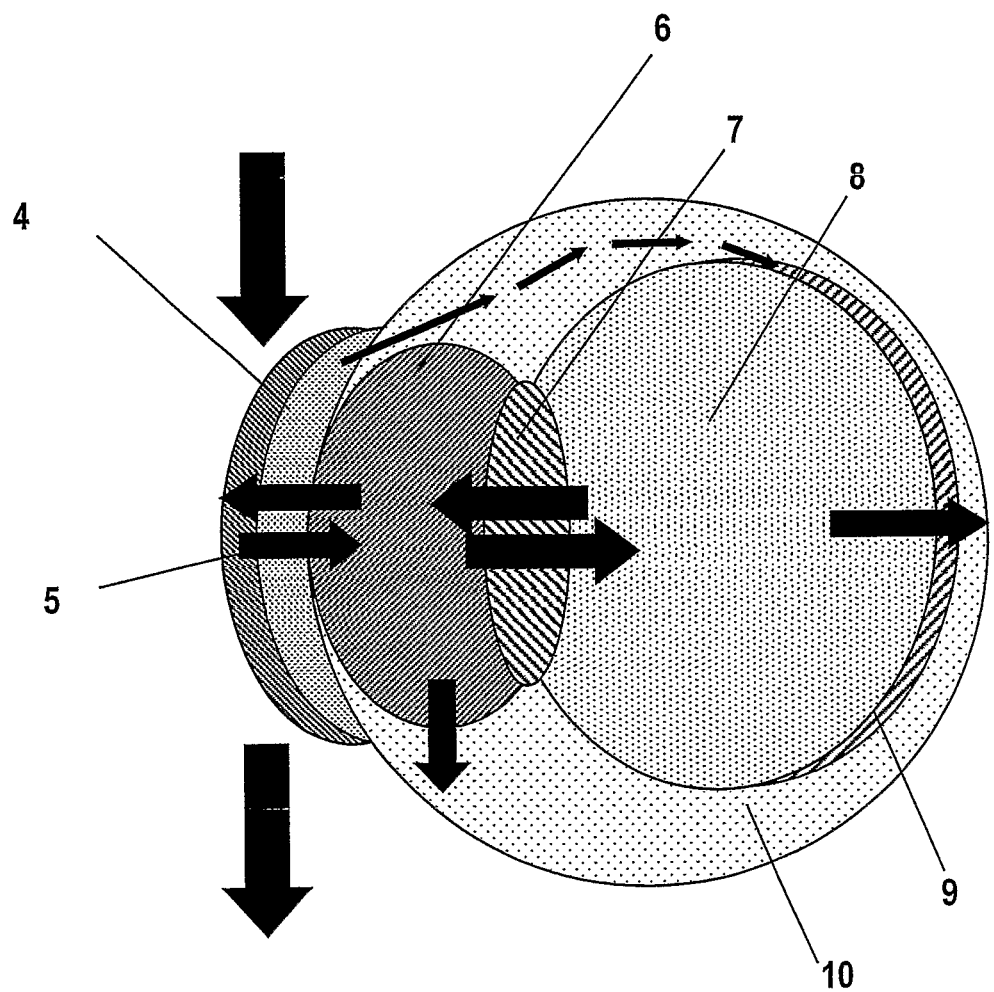
FIG. 15 is a graphical depiction of the pK of the eye. 4 cornea, 5 tear film, 6 anterior chamber, 7 lens, 8 vitrous body, 9 retina, 10 sclera.
Figure 16:
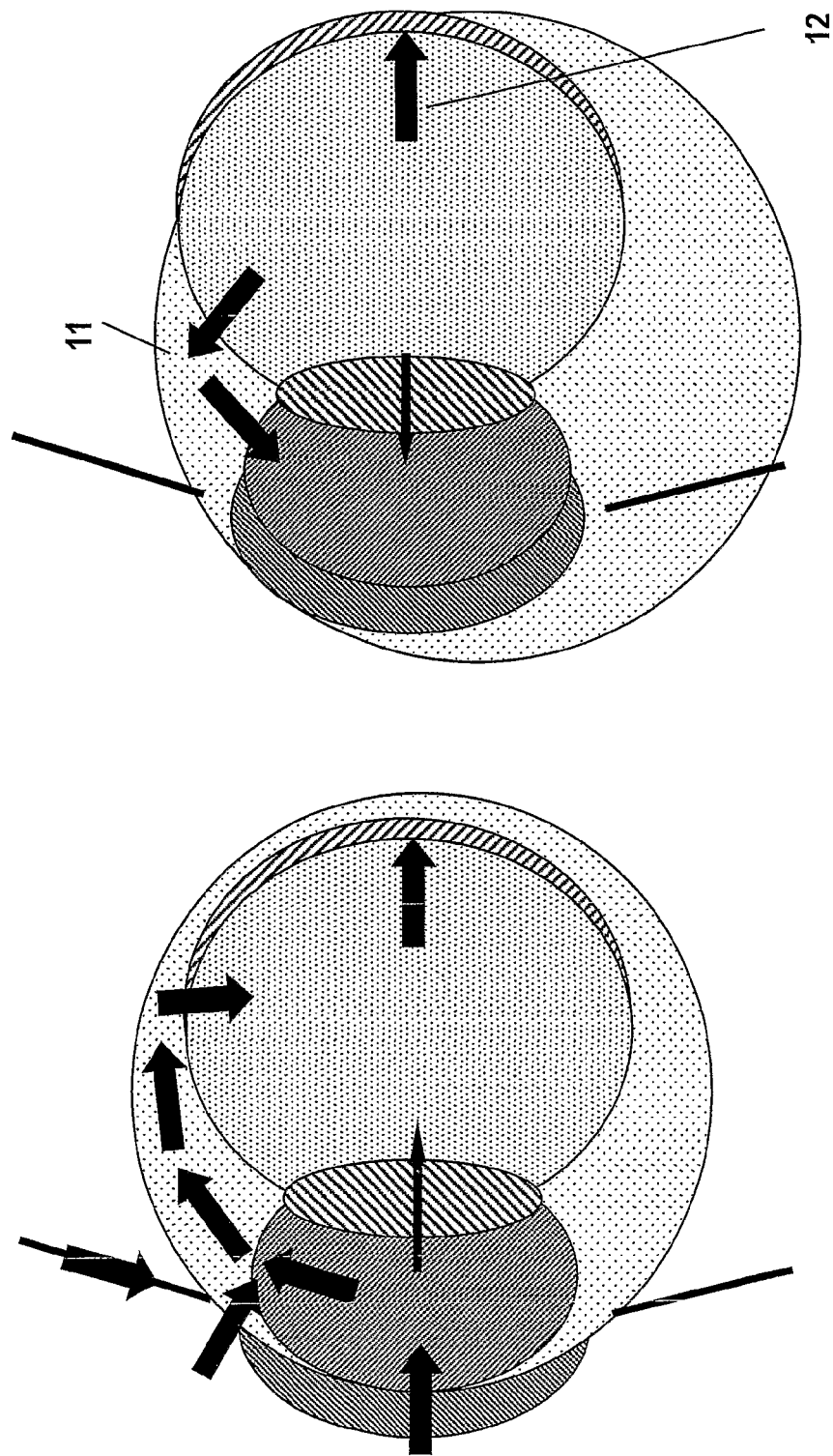
FIG. 16 is a graphical depiction of absorption and elimination routes for ESBA105. 11 hydrophilic drugs, 12 lipophilic drugs.

Human colon adenocarcinoma (Caco-2) cells were seeded on permeable supports of a 24-transwell plate and cultivated during 21 days at 37° C. in a 5% CO$_2$ atmosphere to allow the formation of tight monolayers. Before performing the permeability assay the transepithelial electrical resistance was measured in each well to verify the integrity of the monolayers. Caco-2 monolayers were then washed three times with a saline solution (HBSS) and a mixture containing either 1 μM of ESBA105 with or without caprate, or assay medium alone was added to the upper compartment of the transwells as a control. After defined time points the content of the lower compartments was collected and replaced by fresh assay medium. Samples collected were subsequently analyzed by quantitative ELISA to determine the amount of ESBA105 that penetrated through the Caco-2 epithelial monolayer (FIG. 9).

Example 6

Penetration Through Mouse Jejunum

Approximately 5 cm of mouse jejunum were excised immediately after animal euthanasia and were incubated in oxygen saturated ringer-krebs buffer and flushed three times with ringer-krebs buffer. A section of 3.5 cm was ligated with surgical silk and filled with 200 mcl antibody mixture, containing 1 mg/ml of each antibody format (Infliximab and ESBA105). Approximately 1 cm distal of the everted sac compartment a second ligation was added to secure tightness of the compartment. Everted sacs were placed into a beaker glass containing 10 ml of oxygen saturated ringer-krebs buffer such that only first ligations came in touch with the buffer. Protease inhibitors were added to this receptor compartment to prevent degradation of antibodies. In order to determine amount of each antibody that penetrated through intestinal tissue, 200 mcl probes were taken from the receptor compartment after defined time points and were subsequently analyzed by quantitative ELISA.

Example 7

Topical Application of a Soluble Antigen-Binding Polypeptide

The pharmacodynamics and pharmacokinetics of the topical application of a soluble antigen-binding polypeptide, ESBA105, in rabbit eyes in vivo were studied. Four different formulations were prepared. The first formulation (referred to herein as "B15") was comprised of 9.6 mg/ml of ESBA105 in 0.15M phosphate buffer at pH 6. The second formulation (referred to herein as "B16") was comprised of 10.3 mg/ml of ESBA105 and 0.01% (w/v) chlorhexidine in 0.15M sodium phosphate buffer at pH 6. The first control (referred to herein as "B15-0") was comprised of 0.15M sodium phosphate buffer at pH 6. The second control (referred to herein as "B16-0") was comprised of 0.01% (w/v) chlorhexidine in 0.15M sodium phosphate buffer at pH 6. All formulations were sterilized prior to use, and stored at 4° C. As used herein, "OTT" indicates no treatment.

To study the pharmacodynamics of ESBA105 in the eye, 6 rabbits were used for each formulation. The formulation was tested in both eyes of the rabbits. Two rabbits (4 eyes) were used for each formulation without antibody fragments, and two rabbits (4 eyes) were used as naïve controls. A total of 18 rabbits were used for this study.

The formulations were applied locally to the eyes over the course of six days. Rabbits were treated five times a day, at hour seven, hour ten, hour thirteen, hour seventeen, and hour twenty. On the day of sacrifice, rabbits were treated twice, at hour seven, and hour ten, and sacrificed one hour after the last application.

The eyes were evaluated at day one, day three, and day six. Two rabbits per formulation were used to gather pharmacokinetic data for each time point. An aqueous humour sample and a serum sample were taken at day one and day three. At day six, an aqueous humour sample, and a serum sample were taken and the eyes of the rabbits were dissected into tissues in order to study the distribution of the antibody fragment in the different eye tissues. The results of this study are graphically depicted in FIGS. 11*a* through 11*d*.

Additional studies were performed to study the solubility, pharmacodynamics and pharmacokinetics of ESBA105. The results are recorded in FIGS. 12 through 16. As can be seen from these figures, ESBA105 has been shown to penetrate through corneal tissue layers in rabbits and pigs. ESBA105 accumulates in the vitreous and has a local half time of about 25 hours. The local half time of ESBA105 in the anterior chamber is significantly lower than in the vitreous. Systemic exposure upon topical treatment is extremely low, e.g., approximately 2% of highest local concentration. Further, based on the rabbit topical experiment therapeutic drug levels (approximately 16,000 fold about TNF) can be reached with as little as five topical drops per day. Therefore, topical application of TNF inhibitory scFv antibody fragments could be an effective therapy in diseases located in more posterior segments of the eye, e.g., vitreous, and retina.

Example 8

Dose Response in the Rat Acute Monoarthritis Model

Figure 17:
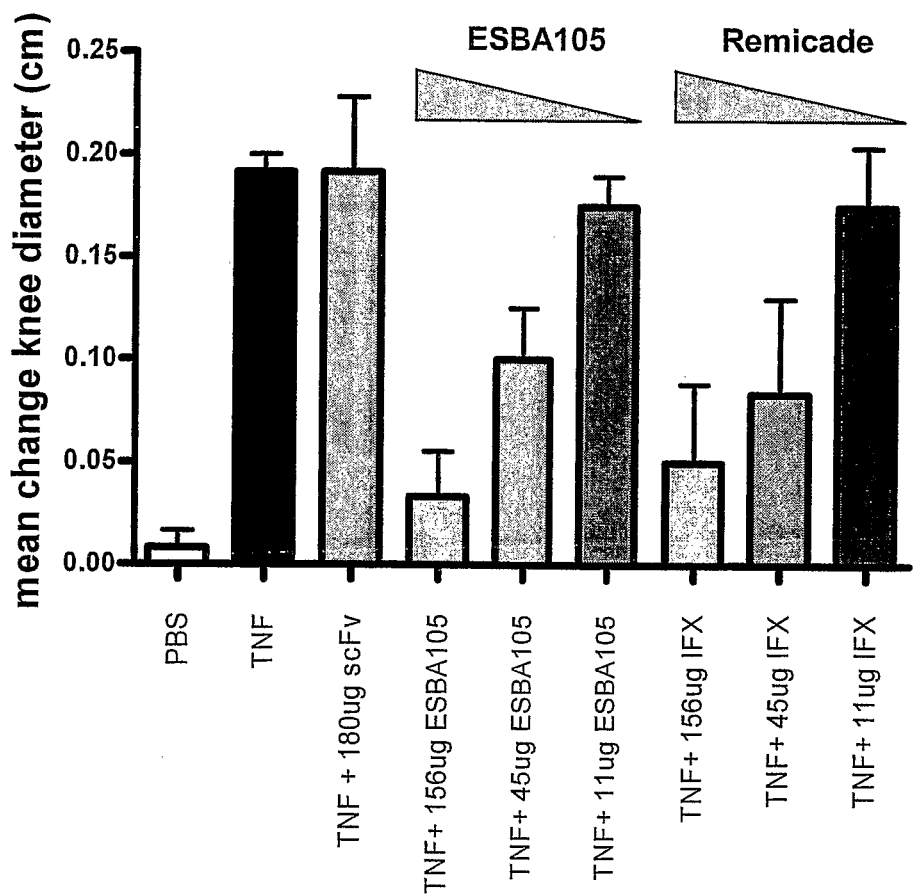

To study the dose response, ESBA105 was administered as shown in FIG. 17. As a comparison, Remicade® (infliximab) was administered as shown in FIG. 17. For this experiment, TNFα was administered with three different dosages (156 µg, 45 µg, or 11 µg) of ESBA105 or infliximab. As controls, PBS, and TNF alone (10 µg i.a.), or scFv alone were used. The results are shown in FIG. 17.

Example 9

Topical Application In Vivo

To determine the maximal systemic exposure and local drug levels during one day of topical administration, one drop every 20 minutes was administered over a period of 10 hours. Drug levels were measured by ELISA in aqueous, vitreous and serum. ESBA105 was formulated as 10 mg/ml in PBS, pH 6.5. For each drop, 30 mcl was applied to the top of the pupil, and the eye lids were then squeezed to remove excess fluid. The results are shown in FIG. 18 and Tab. 2.

Figure 18:
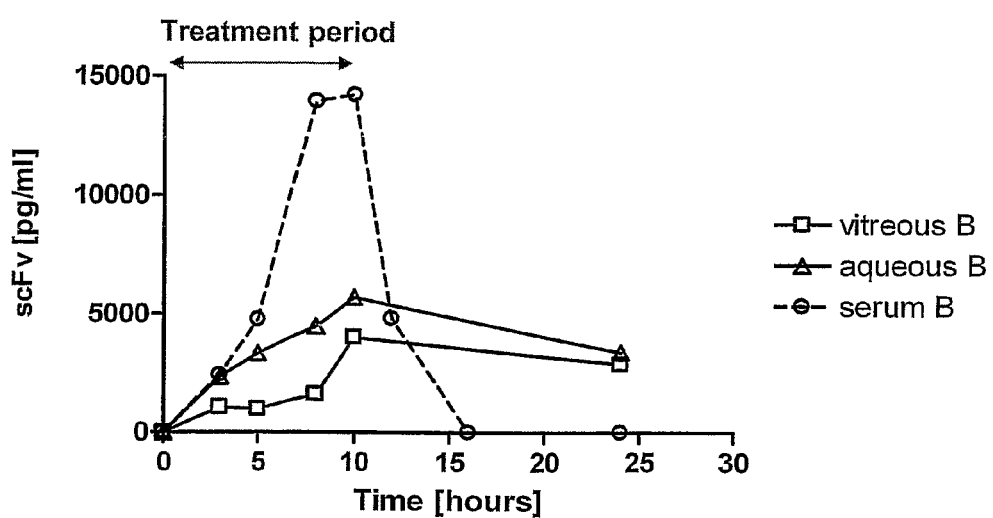
FIG. 18A shows a graphical depiction of topical rabbit eye application in vivo results. Each data point represents the average of two rabbits (four eyes), which received one drop (30 mcl) of 10 mg/ml ESBA105 in PBS pH 6.5 solution every 20 minutes over a maximal treatment period of 10 hours.

TABLE 2 shows the maximal ESBA105 concentrations (Cmax) measured in the indicated compartments in the course of the experiment as described in the legend of FIG. 18 A.

|  | Cmax | cumulative total dose |
| --- | --- | --- |
| Vitr. | 4.0 ng/ml (6.6E–5%) | 9 mg |
| Aequ. | 5.3 ng/ml (1.2E–5%) | 9 mg |
| Serum | 14.2 ng/ml (0.3%) | 9 mg |

The percentage values indicate the percentage of Cmax as compared to the total applied dose (cumulative dose).

Example 10

Topical Application of a Soluble Antigen-Binding Polypeptide

To determine the maximal systemic exposure and local drug levels during chronic topical low frequency treatment, one drop 5 times a day was applied to two rabbits (4 eyes) for up to 6 days. For each drop, 30 mcl of ESBA105 was applied into the lower eye sac (presentation of drug mainly to sclera), full 30 mcl remaining on ocular surface.

The eyes were evaluated after the second drop on day two, day three, and day six. Drug levels were measured by ELISA in aqueous, vitreous neuroretina, choroidea and serum. The results of this study are graphically depicted in FIGS. 19a through 19e.

Table 3 summarizes the median scFv ESBA105 concentrations found after the $6^{th}$ sixth day of administration in the indicated compartments in [ng/ml]

TABLE 3

Median scFv ESBA105 concentrations found after the $6^{th}$ sixth day of administration

|  | Aequeous | Vitreous | Neuroretina | Choroides | Serum |
| --- | --- | --- | --- | --- | --- |
| Median scFv concentration after $6^{th}$ day [ng/ml] | ~100 | ~350 | ~300 | ~100 | <1 |

Numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure may vary substantially without departing from the spirit of the invention, and exclusive use of all modifications that come within the scope of the appended claims is reserved. It is intended that the present invention be limited only to the extent required by the appended claims and the applicable rules of law.

All literature and similar material cited in this application, including, patents, patent applications, articles, books, treatises, dissertations and web pages, regardless of the format of such literature and similar materials, are expressly incorporated by reference in their entirety. In the event that one or more of the incorporated literature and similar materials differs from or contradicts this application, including defined terms, term usage, described techniques, or the like, this application controls.

The section headings used herein are for organizational purposes only and are not to be construed as limiting the subject matter described in any way.

While the present inventions have been described in conjunction with various embodiments and examples, it is not intended that the present teachings be limited to such embodiments or examples. On the contrary, the present inventions encompass various alternatives, modifications, and equivalents, as will be appreciated by those of skill in the art.

The claims should not be read as limited to the described order or elements unless stated to that effect. It should be understood that various changes in form and detail may be made without departing from the scope of the appended claims. Therefore, all embodiments that come within the scope and spirit of the following claims and equivalents thereto are claimed.

REFERENCES

Alberts, B., Johnson, A., Lewis, J., Roberts, K., and Walter, P. (2002). Molecular Biology of the Cell, $4^{th}$ ed.

Alfthan et al., (1995). Properties of a single-chain antibody containing different linker peptides. Protein Eng. 8:725-731.

Altschul, S. F., Gish, W., Miller, W., Myers, E. W. & Lipman, D. J. (1990) "Basic local alignment search tool." J. Mol. Biol. 215:403-410.

Auf der Maur, A., Escher, D., and Barberis, A. (2001). Antigen-independent selection of stable intracellular single-chain antibodies. FEBS Lett 508, 407-412.

Auf der Maur, A., Tissot, K., and Barberis, A. (2004). Antigen-independent selection of intracellular stable antibody frameworks. Methods 34, 215-224.

Auf der Maur, A., et al., Direct in vivo screening of intrabody libraries constructed on a highly stable single-chain framework. J Biol Chem, 277(47): p. 45075-85, 2002.

Benitez Del Castillo, J M. et al. (2004) Long-term treatment of refractory posterior uveitis with anti-TNFα (infliximab). Eye, September 24, e-pub ahead of print.

Binz et al. (2005 October) Nat Biotech 23(10):1257-68

Bird, R E, Hardman, K. D., Jacobson, J. W., Johnson, S., Kaufman, B. M., Lee, S. M., Lee, T., Pope, S. H., Riordan, G. S., and Whitlow, M. (1988). Single-chain antigen-binding proteins. Science 242, 423-426.

Bonfioli and Orefice (2005). Behçet's disease. Semin Ophthalmol 20(3), 199-206.

Boyd et al. (2001). Immunopathology of the non-infectious posterior and intermediate uveitides. Surv Ophthalmol 46, 209-233.

Chothia, C., and Lesk, A. M. (1987). Canonical structures for the hypervariable regions of immunoglobulins. J Mol Biol 196, 901-917.

Chothia, C., Novotny, J., Bruccoleri, R., and Karplus, M. (1985). Domain association in immunoglobulin molecules. The packing of variable domains. J Mol Biol 186, 651-663.

Degim, I. T and Celebi, N. (2007), Controlled delivery of peptides and proteins. Current Pharmaceutical Design, 13, 99-117

Dick, A D. et al. (1997) Immunosuppressive therapy for chronic uveitis:optimising therapy with steroids and cylosporin A. Br. J. Ophthalmol. 81, 1107-1112

Direskeneli (2001). Behçet's disease: infectious aetiology, new autoantigens, and HLA-B51. Ann Rheum Dis 60, 996-1002.

Doring, E. Stigler R, Grutz G, von Baehr R, and Schneider-Mergener J. (1994). Identification and characterization of a TNF alpha antagonist derived from a monoclonal antibody. Mol. Immunol. 31:1059-67.

El-Shabrawi, Y. and Hermann J. (2002) Anti-tumor necrosis factor-alpha therapy with infliximab as an alternative to corticosteroids in the treatment of human leukocyte B27-associated acute anterior uveitis. Ophtalmology 109, 2342-2346

El-Shabrawi, Y. et al. (2003) Anti-tumor necrosis factor alpha treatment in chronic recurrent inflammation of the anterior segment of the eye in patients resistant to standard immunomodulatory treatment. Ann Rheum Dis. 62, 1243-1244

Everekrioglu (2005). Current concepts in the etiology and treatment of Behçet's disease. Surv Ophthalmol 50(4), 297-350.

Giansanti et al. (2004). Infliximab for the treatment of posterior uveitis with retinal neovascularization in Behçet's disease. Eur J Ophthalmol 14(5), 445-448.

Holliger, P. and Hudson, P. (2005), Nat. Biotechnol. 23(9), pp. 1126-1136.

Huston et al. (1988) Proc. Natl. Acad. Sci. USA 85:5879-5883

Johnson, P. H., and Quay, S. C. (2000). Advances in nasal drug delivery through tight junction technology. Expert Opin. Drug Deliv. 2:281-298.

Joseph, A. et al. (2003) Infliximab in the treatment of refractory posterior uveitis. Ophtalmology 110, 1449-1453

Kötter et al. (2003). Human recombinant interferon alfa 2a for the treatment of Behçet's disease with sight threatening posterior or panuveitis. Br J Ophthalmol 87, 423-431.

Lanthier et al. (2005). Infliximab in the treatment of posterior uveitis Behçet's disease. Presse Med 34, 916-918.

Lightman, S., and Kok H. (2002) Developments in the treatment of uveitis. Expert Opin. Invetig. Drugs 11, 59-67

Lindstedt et al. (2005). Anti-TNF-alpha therapy for sight threatening uveitis. Br J Ophthalmol 89(5), 533-536.

Murphy, C C. Et al. (2004) Neutralizing tumor necrosis factor activity leads to remission in patients with refractory non-infectious posterior uveitis. Arch. Ophthalmol. 122, 845 851.

Özen (1999). Vasculopathy, Behçet's syndrome, and familial Mediterranean fever. Curr Opin Rheumatol 11, 393-398.

Ohno et al., (2004). Efficacy, safety, and pharmacokinetics of multiple administration of infliximab in Behçet's disease with refractory uveoretinitis. J Rheumatol 31, 1362-1368.

Perez-Guijo, V. et al. (2004) Tumour necrosis factor-alpha levels in aqueous humour and serum from patients with uveitis: the involvement of HLA-B27. Curr. Med. Res. Opin. 20, 155-157.

Powers C. et al. Pleiotrophin signalling through anaplastic lymphoma kinase is rate-limiting for glioblastoma growth. The Journal of biological chemistry 277(16), 14153-14158, 2002.

Power, W J. Et al. Outcomes in anterior uveitis associated with the HLA-B27 haplotype. Ophtalmology 105, 1646-1651 1998

Reiff, A. et al. (2001) Etanercept therapy in children with treatment-resistant uveitis. Arthrit. Rheum. 44, 1411-1415

Rosenbaum (2004). Blind insight: Eyeing anti-tumor necrosis factor treatment in uveitis associated with Behçet's disease. J Rheumatol 31(7), 1241-1243.

Sakane et al. (1999). Behçet's disease. N Engl J Med 341, 1284-1291.

Schaerer-Brodbeck, C. and A. Barberis, Coupling homologous recombination with growth selection in yeast: a tool for construction of random DNA sequence libraries. Biotechniques, 37(2): p. 202-206, 2004.

Sfikakis, P P. et al. (2001) Effect of infliximab on sight-threatening pan-uveitis in Behcet's disease. Lancet 358, 295-296.

Suhler et al. (2005). A prospective trial of infliximab therapy for refractory uveitis: preliminary safety and efficacy outcomes. Arch Ophthalmol 123(7), 903-912.

Stocks, M. R. (2004). Intrabodies: production and promise. Drug Discov. Today 15:960-966.

Thiel, M A. et al. (2002). Penetration of engineered antibody fragments into the eye. Clin. Exp. Immunol. 128, 67-74.

Tugal-Tutkun et al. (2004). Uveitis in Behçet's disease: an analysis of 880 patients. Am J Ophthalmol 138, 373-380.

Tugal-Tutkun et al. (2005). Efficacy of infliximab in the treatment of uveitis that is resistant to treatment with the combination of azathioprine, cyclosporine, and corticosteroids in Behçet's disease. Arthritis Rheum 52(8), 2478-2484.

Tursen et al., (2003). Evaluation of clinical findings according to sex in 2313 Turkish patients with Behçet's disease. Int J Dermatol 42, 346-351.

Verity et al. (1999). Behcet's disease, the Silk Road and HLA-B51: historical and geographical perspectives. Tissue Antigens 54, 213-220.

Verity et al., (1999b). HLA and tumour necrosis necrosis factor (TNF) polymorphisms in ocular Behçet's disease. Tissue Antigens 54, 264-272.

Ward et al., (1989) Nature 341:544-546 Wechsler et al. (2004). Infliximab in refractory uveitis due to Behçet's disease. Clin Exp Rheumatol 22 (4 Suppl 34), S14-S16.

Winnaker, From Genes to Clones (Verlagsgesellschaft, Weinheim, Germany 1987

Wörn, A., Auf der Maur, A., Escher, D., Honegger, A., Barberis, A., Plückthun, A. (2000). Correlation between in vitro stability and in vivo performance of anti-GCN4 intrabodies as cytoplasmic inhibitors. J. Biol. Chem. 275:2795-803.

Yurdakul et al. (2004). Behçet's syndrome. Curr Opin Rheumatol 16, 38-42.

Zierhut et al. (2003). Immunology and functional genomics of Behçet's disease. Cell Mol Life Sci 60, 1903-1922.

---

The invention claimed is:

1. A composition formulated for topical application to an eye, said composition comprising an antigen-binding polypeptide and a pharmaceutically acceptable carrier, diluent, or excipient, wherein said polypeptide is sufficiently soluble such that it can transit at least one epithelial layer of the eye and into an intraocular space of the eye to achieve an intraocular therapeutic concentration in the absence of a penetration enhancer, wherein the antigen-binding polypeptide comprises the sequence of SEQ ID NO: 13, and wherein the composition has a pH of 6.5.

2. The composition of claim 1, wherein the at least one epithelial layer is an epithelial layer of a cornea.

3. The composition of claim 1, wherein the composition is in the form of eye drops.

* * * * *